(12) United States Patent
Pellionisz

(10) Patent No.: US 8,280,641 B1
(45) Date of Patent: Oct. 2, 2012

(54) UTILITY OF GENOMIC FRACTALS RESULTING IN FRACTALS OF ORGANISMS

(76) Inventor: Andras J. Pellionisz, Sunnyvale, CA (US)

( * ) Notice: Subject to any disclaimer, the term of this patent is extended or adjusted under 35 U.S.C. 154(b) by 962 days.

(21) Appl. No.: 11/975,309

(22) Filed: Oct. 18, 2007

Related U.S. Application Data

(63) Continuation-in-part of application No. 10/630,986, filed on Jul. 29, 2003, now abandoned.

(60) Provisional application No. 60/319,440, filed on Aug. 1, 2002.

(51) Int. Cl.
*G06F 19/00* (2011.01)
(52) U.S. Cl. ......................................................... 702/19
(58) Field of Classification Search .................. None
See application file for complete search history.

(56) References Cited

U.S. PATENT DOCUMENTS

| | | | | |
|---|---|---|---|---|
| 6,920,451 | B2 * | 7/2005 | Shaw | 1/1 |
| 7,366,719 | B2 * | 4/2008 | Shaw | 1/1 |
| 2005/0079524 | A1 * | 4/2005 | Shaw | 435/6 |
| 2005/0158736 | A1 * | 7/2005 | Shaw | 435/6 |

OTHER PUBLICATIONS

Roman-Roldan et al. (1996) Pattern recognition, vol. 29, No. 7, pp. 1187-1194.*
Guo et al. (2002) Chinese Physics, vol. 11, No. 12, pp. 1313-1318.*
Eigen et al. (1988) PNAS, vol. 85, August, pp. 5913-5917.*

* cited by examiner

*Primary Examiner* — Lori A Clow
(74) *Attorney, Agent, or Firm* — Kevin Roe

(57) ABSTRACT

A method and system to analyze repetitive elements of in hereditary material as fractal sets, and analyze and interpret the hereditary information for biological research and medical procedures. The fractal genomic information is analyzed for correspondences to healthy or pathological structural and functional properties of cells, organelles, or organisms. One embodiment of the invention uses analytical tools to analyze and interpret DNA sequences and their aberrant repetitions, fractal defects, of DNA sequences. Various embodiments of the present invention are directed to a method, system, or program for fractal analysis and fractal interpretation of repetitive elements in genomic information for existing and synthetic organisms.

20 Claims, 18 Drawing Sheets

| Repeat Number | | | | |
|---|---|---|---|---|
| 966 | 20 | 40 | 60 | 80 |
| 1 | ATCCGGAAGGCCAGCCCCAGCCCCCAGG | GGGTATGCTGTGTCCGCG | GCGAAGCACCCAGGCTGATTCCCTT | GGGCCGGCAGGTTTAGT | TCGCATGC |
| 2 | ATCCGGAAGGCCAGCCCCAGCCCCCAGC | GGGTATGCTGTGTCCGCG | GCGAAGCACCCAGGCTGATTGCCTT | GGGCCGGCAGGTTTAG | TCGCATGC |
| 3 | ATCCGGAAGGCCAGCCCCAGCCCCCAGC | GGGTATGCTGTGTCCGCG | GCGAAGCACCCAGGCTGATTGCCTT | GGGCCGGCAGGTTTAGT | TCGCATGC |
| 4 | ATCCGGAAGGCCAGCCCCAGCCCCCAGC | GGGTATGCTGTGTCCGCG | GCGAAGCACCCAGGCTGATTGCCTT | GGGCCGGCAGGTTTAGT | TCGCATGC |
| 5 | ATCCGGAAGGCCAGCCCCAGCCCCCAGC | GGGGTATGCTGTGTCCGCT | GCGAAGCACCCAGGCTGATTGCCTT | GGGCCGGCAGGTTTAG | TCGCATGC |
| 6 | ATCCGGAAGGCCAGCCCCAGCCCCCAGC | GGGGTATGCTGTGTCCGCG | GCGAAGCACCCAGGCTGATTGCCTT | GGGCCGGCAGGTTTAGT | TCGCATGC |
| 7 | ATCCGGAAGGCCAGCCCCAGCCCCCAGC | GGGGTATGCTGTGTCCGCG | GCGAAGCACCCAGGCTGATTGCCTT | GGGCCGGCAGGTTTAG | TCGCATGC |
| 8 | ATCCGGAAGGCCAGCCCCAGCCCCCAGC | GGGTATGCTGTGTCGGCG | GCGAAGCAGCGAAGCACCCAGGCTGATTGCCTT | GGGCCGGCAGGTTTAG | TCGCATGC |
| 9 | ATCCGGAAGGCCAGCCCCAGCCCCCAGC | GGGTATGCTGTCGGCG | GCGAAGCAGCGAAGCACCCAGGCTGATTTGCCTT | GGGCCGGCAGGTTTAGT | TCGCATGC |
| 10 | ATCCGGAAGGCCAGCCCCAGCCCCCAGC | GGGTATGCTGTGTCGGCG | GCGAAGCACCCGGCTGAGTGATTTGCCTT | GGGCCGGCAGGTTT-GGTCGCAGT | 1851 |

FIG. 1

```
         10         20         30         40         50
GGACCTGGAATATGGCGAGAAAACTGAAAATCACGGAAAATGAGAAATACACTTTA
         60         70         80         90        100        110
GGACGTGAAATATGGCGAGAAAACTGAAAAGGTGGAAAATTAGAAATGTCCACTGTA
                                   G            T
        120        130        140        150        160        170
GGACGTGAATATGGCAAGAAAACTGAAAATCATGGAAATGAGAAACATCCACTTGA
        180        190        200        210        220        230
GGACTTGAAAATGACGAAATCACTAAAAACGTGAAAATGAGAAATGCACACTGAA
```

Frequency of first, second, third and fourth ranking branchlets (in the reverse order of full development):
6    25    125    625

Frequency of occurrence of hierarchical branchlets in the fractal model of a Purkinje neuronal dendritic tree (Pellionisz, 1989). The number of first, second, third and fourth ranking branchlets is 6, 25, 125 and 625, respectively.

Log-log plotting of frequency against ranking of Purkinje cell dendritic tree branchlets yields the Parabolic Fractal Distribution expressed by the quadratic polinomial of $y = -3.4107 x2 -1.2995x + 2.79608$

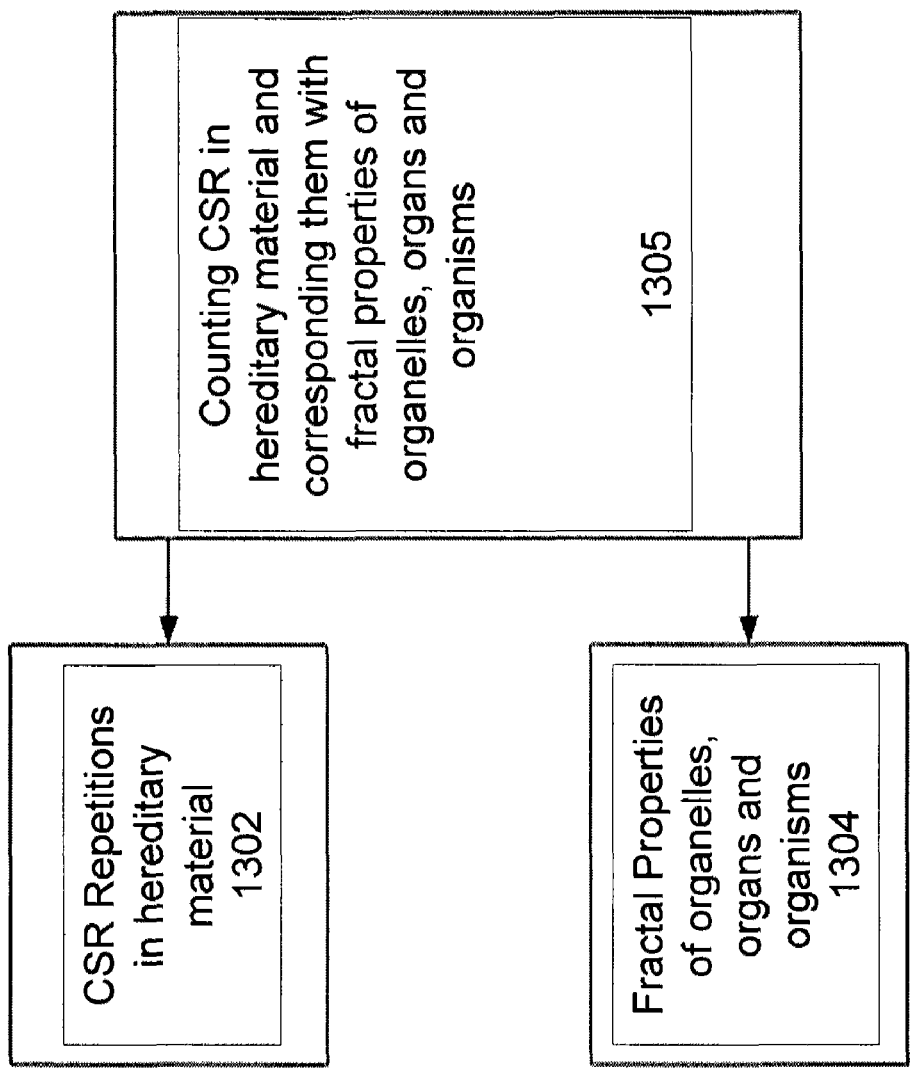
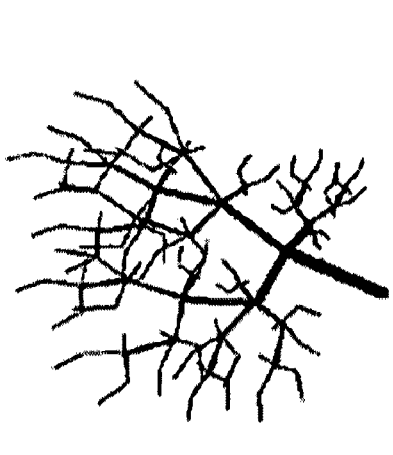
FIG. 13

UTILITY OF GENOMIC FRACTALS RESULTING IN FRACTALS OF ORGANISMS

CROSS-REFERENCE TO RELATED APPLICATIONS

This application (hereinafter referred to as "CIP Application" as defined below) claims priority from a U.S. provisional patent application Ser. No. 60/319,440, filed on Aug. 1, 2002, and entitled: "FractoGene: utility to use self-similar repetitions in the language-like genetic information as fractal sets", by the same inventor and hereby incorporated by reference and hereinafter referred to as the "Provisional Application." It was followed by a U.S. utility patent application Ser. No. 10/630,986, filed Jul. 29, 2003 now abandoned and entitled: "Method and System to Analyze and Interpret Fractal Sets of Genetic Information in Relation to Fractal Sets of Organisms," (hereinafter referred to as the "Parent Application") by the same inventor and hereby incorporated by reference in its entirety.

SEQUENCE LISTING

A Sequence Listing was previously submitted in a three kilobyte file named CRF_Sequence_ASCII_070105.txt on two compact disc copies created on Jul. 1, 2005. The material on these compact disc copies is hereby incorporated by reference.

BACKGROUND OF THE INVENTION

1. Field of the Invention

This invention relates generally to a method and system to analyze, interpret, and distribute the genetic information of any biological organism, either natural or artificially modified or created. It is noteworthy that over the five years from the "Provisional Application" the nomenclature of Genomics has significantly evolved. The use of the word "genetic" today has an extended meaning "genomic" throughout this "CIP Application."

2. Description of the Prior Art

Watson and Crick in 1953 discovered that DNA contains A, C, T, and G base-pairs in a double-helical arrangement. For example, see "A Structure for Deoxyribose Nucleic Acid," *Nature*, by Watson, J. D. and Crick, F. H. C., Apr. 2, 1953, v. 171, p. 737 (1953), which is hereby incorporated by reference. Their discovery immediately shed light on the utility of the double helix in heredity (how the double helix would split and each string of the half base-pairs reconstitute). It also became evident that the sequence of base-pairs is the code of life, but the discovery of the code is not the same as deciphering the code.

Paul Berg in 1980 disclosed a method, by which DNA base-pair sequences composed of A, C, T, and G can be mapped out, such that properties of DNA base-pair sequence could be gradually revealed. For example, see "Biochemical method for inserting new Genetic Code into DNA of simian virus 40: Circular SV40 DNA molecules containing lambda phage genes and the galactose operon of *Escherichia coli*," by Jackson, D. A., Symons, R. H. & Berg, P., *Proc Nat Acad Sci USA* 69, 2904-2909, October (1972), which is hereby incorporated by reference. In the 1990's, The Human Genome Project resulted in a broad genome map, which was deposited into data banks. Sequencing of DNA unveiled, in constantly updated data banks, the raw information about the DNA sequence of several species.

However, no one claimed (and nobody claims even at this time of submission of the "CIP") that the mere mapping of the human genome actually deciphered the code; that is, an explanation was given how the genic and non-genic parts of the DNA, together, as well as the RNA, non-coding RNA, and microRNA systems govern the growth (physiological and pathological) of organelles (such as a single cell), organs (such as the lung) and organisms (such as a bacterium with the smallest DNA of the free living organisms, Mycoplasma Genitalium), let alone a human being. Initially, the human DNA was mapped out in broad detail in 2001 (e.g., see Human Genome Sequencing Consortium: "Initial Sequencing and Analysis of the Human Genome", *Nature*, 409. (2001): 860-921; and Venter, J. C (and 274 co-authors) "The Sequence of the Human Genome", *Science* 291 (2001) 1304-1351), which are hereby incorporated by reference. Nonetheless, while the discoveries of the double helix, and its mapping in 2001, have been impressive achievements, neither provided a means to interpret (decipher) the genetic code itself.

For example, until June of 2007, 98.7% of the human DNA was considered by many scientists to be "junk" DNA or "introns" and other "non-coding sequences"; in this application by "intron" we mean its general definition of all "non-protein coding DNA." Only 1.3% of the human DNA consists of "exons" (e.g., protein-coding DNA, meant in this application in broad terms as "genes"). However, some scientists suspected even at the time of the "Provisional Application" (2002) that most of the non-coding DNA "introns" actually assist gene expression in some way, as their removal is lethal. The ENCODE pilot-results now in 2007 eliminate further "undue experimentation" to establish that the repetitive nature of the "non-coding DNA" and their apparent functionality requires inventions such as it was submitted by the Provisional, Original, and now this CIP Application.

Repetitive Nature of Genomic Nucleotide Sequences

Genomic nucleotide sequences are widely known to contain repetitive segments. There are, however, three different types, that this "CIP Application" improves upon for clarification: "Identical Dispersed Repeats" (hereinafter IDR, or "Identical Repeats"), "Closely Similar Repeats" (hereinafter CSR, or "Close Repeats"), and "Identical Continued Repeats" (hereinafter ICR, or "Runs").

Identical Dispersed Repeats (IDR, or "Identical Repeats")

Nucleotide sequences with identical nucleotides at all positions in the repeated occurrence of said sequences, where the said sequences can be dispersed at any parts of the genome. An example of IDR or "Identical Repeats" is the line 3 occurring also in an identical manner in line 4 in FIG. 1.

Closely Similar Repeats (CSR, or "Close Repeats")

Nucleotide sequences with not identical nucleotides at all positions in the repeated occurrence of said sequences, but permitting up to an including ⅓ of the nucleotides being at variation from the "reference sequence", where the said sequences can be dispersed at any parts of the genome. An example of CSR or "Close Repeats" is all lines except 3 and 4 in FIG. 1, where the "reference sequence" is contained in line 3 or 4, and it is clearly visible that the blacked out nucleotides that are at variation from the reference are less then ⅓ of the total number of the nucleotides in the reference sequence.

Identical Continued Repeats (ICR, or "Runs")

Very short (2-6 nucleotide) sequences with identical nucleotides at all positions, where the repeats follow one another in a continued fashion, at two or more times, on occasion up to hundreds of times. (An example of ICR or "Run" is "CA" re-occur immediately one after the other, or the "GAA" triplet-run that is known to be causing Friedreich' Spinocerebellar Ataxia if the number of triplets is beyond an "acceptable range" (to be defined later)). The importance of distinction between Identical Repeats, Close Repeats and Runs is, that "Identical Repeats" and "Close Repeats" this CIP Application considers as capable of exhibiting fractal organization, while Runs in several instances are known to be the cause of hereditary diseases; and this CIP Application considers them "defects" when inserted into a fractal structure. (The skilled artisan will note that IDR, ICR, CSR are not necessarily mutually exclusive, just like in number theory "odd" and "prime" numbers permit some "odd" number to be "prime"—but not all odd numbers are prime).

FIG. 1 of this "CIP Application" provides a hard-copy reference of IDR and CSR sequences, a copy from the article "Kangaroo, a Mobile Element From Volvox carteri, Is a Member of a Newly Recognized Third Class of Retrotransposons," by Leonard Duncan, Kristine Bouckaert, and David L. Kirk, in Genetics, Vol. 162, 1617-1630, December 2002, which is hereby incorporated by reference. The sequence was duly attached electronically in the format required by USPTO in the Parent Application. The Sequence Listing is submitted in a file named CRF_Sequence_ASCII.txt on a compact disc. The material on this compact disc is hereby incorporated by reference. The above quoted article provides good examples of the highly repetitious nature of DNA in several species. Such repetitions are also present in the 98.7% of the human DNA referred to "junk" DNA. Even from earlier examples it became increasingly evident at the time of inception of the "Provisional Application" that the DNA base-pair sequences are highly repetitious. FIGS. 3, 4, and 5 show, only for illustrative purposes of how the concept of "fractal DNA governing the growth of fractals of organisms" originated, CSR sequences that can be displayed in four lines to show "close similarity" (FIGS. 3 and 4), and it is further illustrated that the first two and second two lines can be joined such that the two halves of the sequence show "close similarity" (FIG. 5).

Some "fractal features" (see the inventor's definitions in Section "Specification") of DNA was recognized in articles, such as "Hints of a language in junk DNA," by F. Flam, Science 266:1320 (1994), and "Linguistic features of noncoding DNA sequences," by Mantegna R N. et al., Physical Reviews Letters 73: 3169-3172, 1994, which is hereby incorporated by reference. These articles were based on the use of fractal geometry, as disclosed in The Fractal Geometry of Nature, by Benoit B. Mandelbrot, W. H. Freeman and Company, New York (1977). Chapter 39, pp. 349-390: "Mathematical Backup and Agenda," is hereby incorporated by reference.

Mandelbrot disclosed mathematics describing elements of nature, coastlines, landscapes, plant arbors, etc. with non-integer (fractal) dimension. For instance, coastlines are lines, yet their dimensionality is not one, as is the case of a straight line, nor does it fill the entire two dimensions of the flat water-surface. (Their dimensionality is a non-integer number somewhere between 1 and 2, depending on how completely the line fills the plane).

Mandelbrot investigated the relationship between fractals and nature using the discoveries made by Gaston Julia, Pierre Fatou and Felix Hausdorff, (see The Fractal Geometry of Nature, Freeman, revised edition (1983)), which is hereby incorporated by reference. Mandelbrot disclosed that many fractal patterns existed in nature, and that fractal analysis could accurately model some natural phenomena. He also introduced new types of fractals to model more complex structures like trees or mountains. By furthering the idea of a fractional dimension, Mandelbrot made fractals a very rich field of analysis.

In addition, information that distinguishes one fractal set from another is contained in a "residue" left over after iterated function systems have been employed to compress the data in the sets. For computation, this "residue" is often the most important element. Compression makes fractals ideal for genetic code encapsulation of the intricate features of complex organisms that would otherwise require more information than the DNA is capable of coding if separate (uncompressed) information were used. One example of such intricacy would be the specification of each branchlet of the neurons in the brain (numbering approximately 10 to the 12 exponential power).

Efforts to sequence the genome have relied on a map-based approach, because over 50 percent of the genome in higher mammals (up to 98.7% in the human genome) is repetitive. So many parts of the genome look similar to other parts (of the genome) that if you only work with small pieces of genetic code, it is tempting to try to stick similar pieces from different parts together. "The physical map allows us to work with large pieces and to know where the little ones are supposed to go," according to John D. McPherson, co-director of the Washington University Genome Sequencing Center.

For several years it has been suspected, that junk DNA may not be junk after all. (Quoted from Gene exchange #2, 1996). Although 98.7% of the DNA in human DNA does not obviously code proteins, and appears to consist of "meaningless" repetitive sequences, the possibility that this useless DNA has some unknown function has fascinated scientists.

It is well established that intron and other non-coding sequences DNA sequences regulate gene expression in positive and negative ways, provide post-transcriptional regulatory options, and provide structure among other functions. However, the problem of how introns, together with the exons, could be used to understand the meaning of the coded DNA message has previously been unresolved.

More than 95 percent of DNA is called "junk DNA" by molecular biologists, because they are unable to ascribe any function to it. However it has been found that the sequence of the syllables is not random at all and has a striking resemblance with the structure of human language. Therefore, scientists now generally believe that this DNA must contain some kind of coded information. But the basic concept of the code and its function is still largely unknown. It has been speculated that this region of DNA may contribute to the cellular processes, such as regulation of transcription. Therefore, deciphering the information coded in the regulatory regions may be critical to the understanding of transcription in a genomic scale. Yet the development of computational tools for identifying regulatory elements has lagged behind those for sequence comparison and gene discovery. Former approaches to decipher regulatory regions use co-regulated genes and then find a pattern common to most of the upstream regions.

SUMMARY OF THE INVENTION

The present invention provides a method and system to analyze and interpret the correspondence between the fractal structure of DNA and the fractal property(s) of organism(s). The invention can be implemented in numerous ways, such as by a mathematical method, a computer software, embedded applications, one or more genome databanks with fractal analysis or a program stored on electronically-readable media. Other implementations, while not listed here are included in this application. Three aspects of the invention are described below. The first and second have "new material" added compared to the "Parent Application." Since the core of the invention is that DNA fractals are in a causal relationship with fractals found in resulting organisms, as part of the "new material" the method is shown in detail how to establish that the DNA is fractal; that is, its individually different repetitive sequences follow the Zip—Mandelbrot Parabolic Fractal Distribution Law. This "new material" is an improvement of the invention of relating DNA fractals to Fractals of Organisms as it provides further mathematical methods of the analysis of DNA fractals.

A first aspect of the invention is directed to a method to analyze and interpret information inherent in hereditary material of one or more organisms in terms of one or more fractal sets, in relation with a resulting fractal structure and function of said one or more organisms, such that said one or more fractal sets are defined as a superposition over at least two iterations of a fractal template. As "new material," the analysis and interpretation includes the correlation of "fractal complexity" of the organism with the number of repetitions in the hereditary material.

A second aspect of the invention is directed to a method of fractal diagnosis of one or more diseases of an organism associated with aberrations of fractal sets of DNA, wherein the fractal diagnosis includes an experimental correlation of a first plurality of aberrant numbers of repetitive DNA sequences and a second plurality of aberrant number(s) of repetitive structures in the organism. The fractal diagnosis includes detection of "fractal defects" (for instance, tri-nucleotide runs distancing closely similar repetitive DNA sequences, such at least one of the closely similar repetitive element is defective by the insertion of sequence that does not belong with the fractal structure).

A third aspect of the invention is directed to a system to analyze the correlation of one or more fractal sets of DNA of an organism and one or more fractal sets of structures in the organism by measuring a fractal dimension and one or more fractal properties of one or more DNA sequences and associating the fractal dimension and the one or more fractal properties with a fractal dimension and one or more properties of a plurality of structures in the organism.

These and other objects and advantages of the invention will become apparent to those skilled in the art from the following detailed description of the invention and the accompanying drawings.

BRIEF DESCRIPTION OF THE DRAWINGS

FIG. 1 illustrates repetitive DNA of an organism, with a portion of DNA identified as SEQ. ID. NO. 1 in the CRF file included with the application.

FIG. 4 illustrates repeats in the genetic code of an organism, with a portion of DNA identified as SEQ. ID. NO. 2 in the CRF file included with the application.

FIG. 5 illustrates re-arranged repeats in the genetic code of an organism, with a portion of DNA identified as SEQ. ID. NO. 2 in the CRF file included with the application.

FIG. 13 provides a flowchart with illustrative examples, for a method to correspond CSR Repetitions in hereditary material with fractal properties, such as fractal complexity, fractal components, etc. of an organism, in this case a Purkinje cell, in accordance with one preferred embodiment of the present invention, with a portion of DNA identified as SEQ. ID. NO. 2 in the CRF file included with the application.

DETAILED SPECIFICATION OF THE PREFERRED EMBODIMENT

Genomic and Fractal Terms

Figure 2:
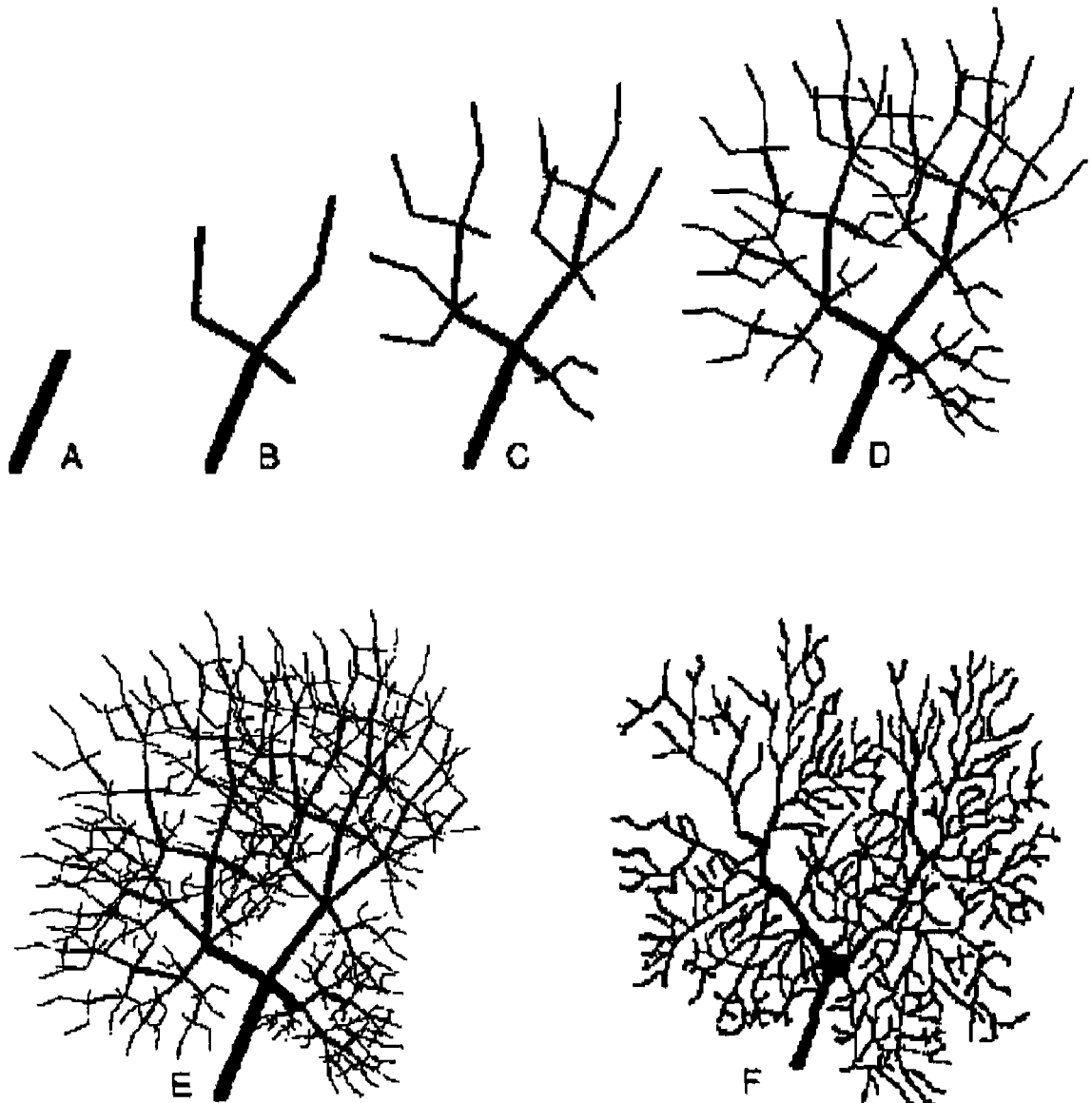
FIG. 2 illustrates a fractal model of the Purkinje neuron, as shown in a 1989 article by Pellionisz, A. *Neural Geometry: Towards a Fractal Model of Neurons*, in: R. M. J. Cotterill, *Models of Brain Function*.

Since the state of the art of Fractals as well as Genomics are rich and are rapidly expanding, various authors use "Fractal terms", as well as "Genomic terms" in somewhat different sense. Thus, in the section below definitions are provided of the terms of this "CIP Application."

Genomic Terms

"Genomic terms" are changing, as reflected for instance by the U.S. led international ENCODE study results (Birney et al., Nature, June 2007, 14: 447 (7146): 799-816), which hereby incorporated by reference. It is realized that the former distinction between "gene" (limited to contiguous sequences) and "genome" (the full sequence) is not as simplistic as formerly thought. Thus, the term "gene" is used meaning "hereditary material" (including protein-coding and non-coding DNA and RNA, etc). Also, it is increasingly realized that no species are likely to be characterized by a single "full nucleotide sequence"—but copy number variations, insertions and deletions (etc) are much larger among specimens a single species than originally thought. This "common knowledge" of today is fully consistent with the teaching of the earlier "Provisional Application" and "Parent Application", in which it was an explicit requirement that a statistically significant number (>100) fully sequenced genomes are needed for comparisons of genomes of individual specimen. Presently (not covered by this "CIP Application") a massive effort is exerted to make full genome sequencing economically feasible for populations. Likewise, the earlier "Provisional Application and "Parent Application" referred to a "healthy range" of e.g. repetitions of genomic sequences. Realizing that this term is dynamic in time as the discovery process of genome function continues, instead of referring to "healthy range" of repetitions of genomic sequences the improved term "acceptable range". "Acceptable Range" is defined as the number of one or more Identical Continued Repeats (ICR-s) of DNA sequences at particular loci in the full genome that is not associated with one or more pathological conditions by the preponderance of evidence of PubMed referenced publications of said organism at the time of the use of the term "Acceptable Range."

Fractal Terms

Definition of Fractal terms as used in this "CIP Application" follows. Mandelbrot conceptually defined a fractal as a rough or fragmented geometric shape that can be subdivided in parts, each of which is approximately a reduced-size copy of the whole.

Fractal

"Fractal" is mathematically defined henceforth according to Mandelbrot: "Fractal" is mathematically defined as any object for which the Hausdorff dimension is greater than the topological dimension" (as defined in *The Fractal Geometry of Nature*, by Benoit B. Mandelbrot, W. H. Freeman and Company, New York (1977). Chapter 39, pp. 349-390: "Mathematical Backup and Agenda") is hereby incorporated by reference.

Fractal Template

"Fractal Template" is defined as the basic irreducible element of a recursive process in a fractal. For instance in the Lindenmayer L-string replacement recursive iteration the "Fractal Template" is the basic structural pattern (see FIG. 5.B) that serves as the unit of L-string replacements, defined as the "Fractal Template" of the Lindenmayer fractal.

Fractal Set

"Fractal Set" is defined as a superposition over at least two iterations of a fractal template.

Fractal Distribution

"Fractal Distribution" is defined as any set of Identical Dispersed Repeats (IDRs), when the occurrence of IDR-s plotted against their rank (most frequently occurring element to least frequently occurring element) of said elements follow the Zipf-Mandelbrot Parabolic Fractal distribution law, as defined on page 77 of *"Fractals in Biology and Medicine"*, Volume II see equation (1) below (see pp. 77, equation 13), Volume I. page 55-77 for the Paradigm (see pp. 55-57. For the computation, Volume IV, page 55-77 is cited (Birkhauser, 1997) by G. Losa, T. Normenmacher, D. Merlini, E. R. Weibel, which is hereby incorporated by reference (page 77, lines 4-6 read: " . . . it was possible to estimate the corrected fractal dimension (FD). All images were successively analysed using BENOIT 1.3 (TruSoft Int'l Inc. 204 37$^{th}$ Ave, N#133. St Petersburg, LF 33704), a commercially available program." The referenced Zipf-Mandelbrot parabolic fractal distribution curve, mathematically defined by equation (1) below is:

$$p(r)=(k+r)-df \qquad (1)$$

where p(r) is the probability of occurrence of a given element with rank r, and k, d, and f are positive constants.

The mathematics is also available in the other material incorporated by reference on page 32 of Sumiyoshi Abe and Yuko Okamoto "Nonextensive Statistical Mechanics and Its Application. Lecture Notes in Physics" (Vol. 560, edited by Sumiyoshi Abe and Yuko Okamoto, published by Springer-Verlag, Berlin, New York, ISBN 3-540-41208-5, 2001, see Abe Okamoto "Nonextensive Statistical Mechanics" page 32, equations 80-81. The Zipf-Mandelbrot Law provides another quantitative measure of fractals. In addition to fractal dimension, defined and computed by material incorporated by reference of Mandelbrot's landmark book (see pages 94, 193, 303) to quantitatively establish statistically significant correlation of fractals. How to measure fractal dimension, e.g. by the "box method", is well known in the prior state of the art, even with commercially available canned software available (BENOIT Fractal Analysis Software by TruSoft, Florida). Another well known skill in the prior art to quantitative measure to relate fractals is to use statistical correlation of two or more fractals by their curves of Zipf-Mandelbrot distribution. How to do this is based on first measuring the Zipf-Mandelbrot distribution of each, according to equation (1) above, also expressed by equation (80) under the heading "3.5 Zipf-Mandelbrot Law", pp. 32 of the Sumiyoshi Abe and Yuko Okamato book. The step of measuring fractal properties such as fractal dimensions and Zipf-Mandelbrot distribution in each fractals was the well-known prior state of the art. Leaders of the art of Fractal Analysis stated that the prior art in the Chapters in "Fractals in Biology and Medicine, Vol. I. pp. 55-77. as follows (fractals in biology and medicine volume one). On page 55, in the Chapter titled "Fractal Landscapes in Physiology &Medicine: Long-Range Correlations in DNA Sequences and Heart Rate Intervals" starting at the second paragraph of the Abstract states, "We briefly review recent work from our laboratory concerning the application of fractals to two apparently unrelated problems: DNA organization and beat-to-beat heart rate variability". The prior state of the art was reversed by replacing the concept of "unrelated" by the novel concept of "statistically correlated". Thus, in addition to the two arts prior to Application (1) Fractal Analysis of DNA and (2) Fractal Analysis of Properties of Organisms (in their case, the beating of the heart), two further arts had to be inserted; (3) Correlation Analysis, together with (4) Statistical Analysis. According to Sumiyoshi Abe and Yuko Okamoto, "Nonextensive Statistical Mechanics and Its Application. Lecture Notes in Physics", Vol. 560, edited by Sumiyoshi Abe and Yuko Okamoto, published by Springer-Verlag, Berlin, New York, ISBN 3-540-41208-5, 2001, equation 80 on page 32 (Abe Okamoto Nonextensive Statistical Mechanics p 32), which is hereby incorporated by reference (elaborating on the Zipf-law as extended by himself to the Zipf-Mandelbrot Parabolic Fractal Distribution Law), "Mandelbrot suggested that such behavior was reflecting a kind of fractality hidden in the problem." (See middle line in page 32 of the Sumiyoshi Abe and Yuko Okamoto book, on "Nonextensive Statistical Mechanics and Its Application" (Abe Okamoto). Both Correlation Analysis and even Nonextensive Statistics were well-known skills in the prior art, to the extent that "nonextensive" could be demonstrated in said book (see Abe Okamoto) in 277 pages, with 201 equations and 277 references in just one of its chapters (cited in the material incorporated by reference), where in Table 1 the "Power law interactions" (page 88) are also defined by three of the additional 16 equations. It is noteworthy, that because this mathematical distribution originated from linguistics and economics, it is also known as the "Pareto-Zipf Law," e.g. Reed, W. J. (2001) The Pareto, Zipf and other power laws, Economic Letters, 74, 15-19, which is hereby incorporated by reference. (Pareto) William Reed (Department of Mathematics and Statistics, University of Victoria, Canada), provided six complex equations (A1-A6) on how to use power law statistics. The first sentence of (Pareto) reads "Many empirical distributions encountered in economics and other realms of inquiry exhibit power-law behaviour", and on the next page William Reed states, "I claim, a simple, plausible explanation which has apparently been overlooked and which can explain many examples in economics (including the Pareto and Zipf laws) and other areas. This is outlined below". The Patent Application teaches "how to compare power law curves" (Pareto) by W. Reed's equations (A1-A6) that compare in (Pareto) power law curves. The present application applies the equations not for economics, but for DNA and the growth DNA governs, that shows how such distributions and statistically correlated fractal analysis of structuro-functional properties, also showing power law distribution curves. The method of establishing fractality of DNA by the Zipf-Mandelbrot Parabolic Fractal Distribution is detailed below.

Fractal Dimension

"Fractal Dimension" is hereby defined as follows. Beyond the above mathematical definitions, a method is specified to actually measure "Fractal Dimension" in preferred embodiments. Skilled artisans are familiar with the box counting method. The state-of-art box-counting method involves counting non-empty artificially defined boxes in the image (areas having small dots) for various patterns such as straight lines, irregular curves, and geometric shapes. Consider a straight line that consists of a uniform distribution of $N_0$ points along the one-dimensional horizontal line in a three-dimensional space. Small cubes with dimension d are then used to cover the straight line (one can also use small spheres of radius r). The minimum number of such cubes $N(d)$ to cover the points of a straight line is inversely proportional to d (i.e., the smaller the value of d, the greater number of cubes is required):

$$N(d) \sim 1/d \quad (2)$$

Similarly, for a line with points distributed on a two-dimensional surface in three-dimensional space, the minimum number of cubes required to cover the line is inversely proportional to $d^2$ (i.e., on the two-dimensional surface, as the cube face area decreases, more cubes are needed). In other terms, the minimum number of cubes to cover the set will scale in accordance with the following law:

$$N(d) \sim 1/d^2 \quad (3)$$

The dimension of the scaling law is defined as follows:

$$N(d) \sim 1/d^f \quad (4)$$

To define a capacity dimension f, equation (3) may be written as:

$$f \sim \log N(d)/\log(1/d) \quad (5)$$

with: $N(d) \rightarrow \infty$ and $D \rightarrow 0$.

Fractal Complexity

"Fractal Complexity" is hereby defined as follows. Since for hereditary material, such as DNA, and for organelles, organs and organisms that the hereditary material governs, there are various methods of calculation of "Fractal dimension" that are not always transparent. Therefore, descriptor adjectives such as "fractal complexity", "fractal components", "fractal structures", "fractal properties" and "fractality" are also explained below. "Fractal Complexity" is an emergent property of fractals, see the Fractal Model of Purkinje Neuron in FIG. 2., defined as the hierarchical number (not the total number of parts) of how many subsequent recursion in the L-string replacements occurred. Looking at FIG. 2, it should be clear that Fractal Complexity of B=1, C=2, D=3 and E=4, as each branchlet of B was replaced by the pattern of B to yield C, thereby increasing the Fractal Complexity of B=1 to C=2. It is noteworthy that while from B to E the Fractal Complexity increases from 1 to 4 (The Fractal Complexity is a function of fractal growth) while the "Fractal Dimension" at each level is the same (Fractal Dimension is a constant of throughout the growth of a fractal).

Fractal Structure

"Fractal Structure" is defined in this CIP Application as any structure that can be mathematically modeled by a Fractal.

Fractal Function

"Fractal Function" is defined in this "CIP Application as any function that can be mathematically modeled by a Fractal.

Fractal Components

"Fractal Components" is defined as follows. Since at each hierarchical level of L-string replacements each branchlet at "hierarchical level n" is replaced by the entire "Fractal Template", the number of dendritic segments grows according to a power function with the subsequent steps of replacement. The Fractal Model of the Purkinje cell (see FIGS. 2 and 3) shows "Fractal Complexity" level 1-4, and it will be shown in FIG. 9 that the actual numbers of Fractal Components" are increasing parabolically from 6 to 625 in the number of the branchlets. It follows from the Zipf-Mandelbrot Parabolic Fractal Distribution law that the "Fractal Components" constitute a "Fractal Set".

Fractality

"Fractality," therefore, is an umbrella term in this CIP Application, referring to any/all of the above defined features exhibited by an object.

Fractal Properties

"Fractal Properties" are described as characteristics (for instance, the pattern of dendritic arbor of brain cells) of fractal objects.

Fractal Properties

"Fractal Structural Property" is described as structural characteristics (for instance, the pattern of dendritic arbor of brain cells) of objects with fractality.

Fractal Modeling

The "Fractal Modeling" of the Purkinje neuron in FIG. 2 was done by Pellionisz, 1989, (e.g., see FIG. 2., Fractal Model of Purkinje Neuron by Pellionisz, from *Neural Geometry: Towards a Fractal Model of Neurons*, pp. 453-464, in *Models of Brain Function*, by R. M. J. Cotterill, Cambridge Univ. Press, 1989, was is incorporated by reference). For the mathematical basis, see the Lindenmayer method at "*CRC Concise*

*Encyclopedia of Mathematics*", (Chapman and Hall, 2$^{nd}$ Edition, 2003) by Eric W. Weisstein, p. 1766, which is hereby incorporated by reference.

Fractal Complexity

The Fractal Model of Purkinje neuron illustrates the definition of the term "Fractal Complexity." In each step on FIG. 2B to FIG. 2E (and FIG. 3B to FIG. 3E), an emerging pattern is developed based on an initial structure, defined as "Fractal Template" on FIG. 3B. Mandelbrot suspected in 1977 that fractals might apply to neuron branching (p. 162, ibid), but he wrote "the notion that neurons are fractals remains conjectural." Nonetheless, Pellionisz in 1989 published a fractal model of the Purkinje neuron of the brain, thus disclosing that body organs and organelles, even at a microscopic brain-cell level, can be viewed as fractal sets, even though the genetic mechanism of doing so was unknown at that time.

Inverse Problem of Fractals

"Inverse Problem of Fractals" is defined as follows. Generating a fractal is straightforward process, using a recursive algorithm, such as the L-string replacement, that iterates the Fractal Complexity to an ever higher level. Iterated function systems, such as the Lindenmayer L-string replacement method, provides the basis for efficient data compression and decompression. It is of particular importance that fractals can be generated (by means of repetition of the fractal template), or inversely, a complex fractal can by deduced to its fractal template.

While generating a fractal e.g. by the Lindenmayer L-string replacement method is straightforward, the so-called "inverse" problem, to deduce the fractal template from a complex fractal, was previously a formidable problem, until Barnsley and his co-workers provided a solution: Barnsley, M. F., Ervin V., Hardin, D. and Lancaster, J.: "Solution of an inverse problem for fractals and others sets", *Proc. Natl. Acad. Sci. USA*, 1986, Vol. 83, pp. 1975-1977 which is incorporated by reference. (Solution of an inverse problem for fractals Barnsley et al pnas00311-0018) The parent patent application utilizes the methods of said material incorporated by reference, well known to the artisan skilled in fractal analysis, to reduce structural properties of biological structures to fractal sets, where biological structures include both organelles (such as leaves), organs (such as lung), or organisms (such as the smallest free-living organism, mycoplasma genitaliae), as well as include genomic sequences of the hereditary material, and by reversing the teaching of the prior state of the art that they are unrelated, states that the fractal sets of sequences of hereditary material and the fractal sets grown by them are statistically correlated, greatly simplifying the prior state of the art. On page 1975 of said material incorporated by reference, (Solution of an inverse problem for fractals Barnsley et al pnas00311-0018) authors provide enablement in their first sentence (page 1975, right below the Abstract): "We present an application of the contraction mapping principle which yields succint descriptions, approximations, and reconstructions for complicated sets such as fractals and biological structures".

Figure 3:
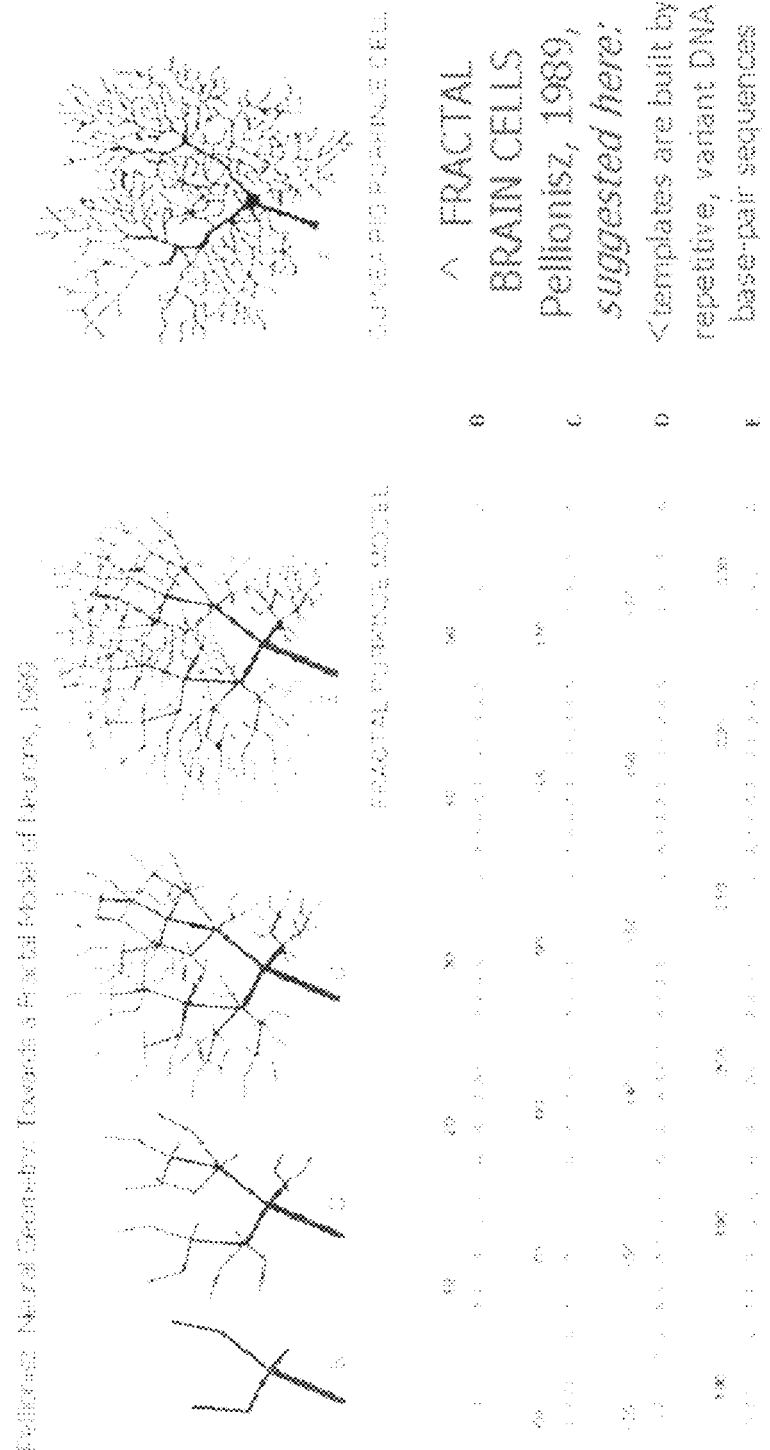
FIG. 3 illustrates a complete circle between the demonstrably fractal neuron of Purkinje cell model, the demonstrably fractal sequences of a guinea pig Purkinje cell) and a repeated sequence of DNA base pair, with a portion of DNA identified as SEQ. ID. NO. 2 in the CRF file included with the application.

Further on the right side of page 1976, their FIG. 3. displays the fractal structural properties of a biological organism (leaves of a black spleenwort fern, reduced to fractal sets: "FIG. 3. Model of a black spleen obtained by application of the collage theorem (page 1976). The four affine transformations are specified in Table I. (page 1977)" They (M.F.B.) provide in said material incorporated by reference (page 1975) the mathematical proof of the method: see in their page 1975 right bottom corner section "Here we present a method for obtaining approximate solutions of the inverse problem . . . COLLAGE THEOREM". The method is elaborated (see page 1975, the middle of right column), not only in equations but also in how it is implemented by a microcomputer: "When K C R", it can occur that the Hausdorff-Besicovitch dimension of s/ is noninteger (5), in which case ds is a fractal as defined byMandelbrot (1). The attractor sl of an IFS can be calculated as follows (5). Let p>0 denote a probability vector p=(Pi, P2, . . . *, PN) with each Pi>0 and Ypi=1. Start from x0 E K and define a sequence {x"j by choosing successively xn E {W(xn–1), W2(xn–1), . . . , WN(X.–1)} (n=1, 2, 3, . . . ), where probability pi is attached to the choice xn=wi(xn-1) once Xn–1 has been chosen. Then si={y: there is a subsequence xnj y). Observe that a E sl if and only if each open neighborhood of a contains infinitely many elements Xn. When K=[0,1]×[0,1] C R2, such a computation is readily effected and displayed on a microcomputer by plotting, say, {x": n=51, 52 . . . 500,000}. In fact, the points xn will approach a distribution given by the unique probability measure (,t on K), which is stationary for the discrete-time Markov process in which the probability of transfer from x E K to a Borel subset R of K is P(xa)=lPiswxx) (90; see ref 5. We call, u the p balanced measure for the IFS {Kwm: i=1, 2, . . . , N}. The support of u is s independent of p>0. "Table I. of this material is incorporated by reference, see right upper corner of (see page 1977) which shows that the structural fractal properties in the prior state of the art of the parent patent application need not (in fact cannot) be "defined", but e.g. the 28 parameters of the fractal properties of the shape of fern leaves are not "defined", but "mined" by their method. To further clarify, a simple citation included from the widest known book of the founder of the art of Fractal Analysis; *The Fractal Geometry of Nature* by Benoit B. Mandelbrot, W. H. Freeman and Company, New York (1977) (Mandelbrot fractal geometry of nature). On page 1, from the first paragraph, it is stated "Clouds are not spheres." (but fractals). Do clouds have fractal structural properties?Most certainly. But an infinite number of properties, as even the most rudimentary "fractal structural property", the fractal dimension, greatly varies (with the size of the box applied to measure it). Another classic "fractal structural property" (again, from the material incorporated by reference, see Mandelbrot fractal geometry of nature page 25) is the "length of coastline" of e.g. Britain. Even such a fractal structural property as length is not "defined", but rather "measured" (and the length of the coastline is a function of the length of the yardstick used to measure it). Later, Barnsley and coworkers elaborated their solution in the field of visual data compression (an art very different from the DNA, the subject matter of the present application); (e.g., see U.S. Pat. No. [4,941,193, 5,065,447, and 5,347,600], to Barnsley et al.; and U.S. Pat. No. 5,754,704 to Barnsley, which are incorporated by reference).

Basic Accomplishments of Preferred Embodiment by Mathematical Fractal Methods

Previously, there was no relationship attributed to repetitions of hereditary material and repetitions of structural and functional properties. The embodiment of the invention of relating in terms of mathematical methods, software systems, embedded hardware, etc. enables relating fractal complexity, fractal dimensions and other fractal properties of hereditary material and the organisms they govern.

No previous explanation could provide a mathematically solid basis for utilizing lessons drawn from the evolution of hereditary material. This disclosure claims that with phylogenesis (and ontogenesis that mimics it) goes through an ever-increasing fractal refinement of adding "improvements" (in the form of CSR sequences) to the relatively slowly increasing repertory of exons (in former terminology "genes"). By putting numerical measures by means of counting and sorting CSR "Close Repetitions" in the DNA as Fractal Sets and their mathematical counting and analysis, an alternative preferred embodiment of this invention provides a software and/or hardware tool to use cross-species platforms to compare different animal (and human) fractal models, both at the level of DNA sequences, as well as in differentiation of the fractal sub-cellular organisms, cells, organelles and full organs (e.g. pulmonary bifurcations) of organisms.

The present invention applies the concept of fractals to analyze and interpret the causal relationship of the fractal properties of DNA (such as repetitive DNA sequences where the occurrence over the ranking of such elements follow the Zipf-Mandelbrot Parabolic Fractal Distribution) to the fractal properties of living organisms (such as repetitive arbor of brain cell dendrites) including but not limited to bacteria, plants, animals, and humans, such as rice, ferns, trees, and animal or human neurons, and so forth, including both natural organisms already in existence, and those modified and created in the future. Most fractals have extremely great complexity and detail, thus it is also possible to use fractals to design small size molecules and structures (e.g. biotechnology, protein-based nanotechnology, bio-computer technology, and so forth).

Methods of fractal analysis applications that were disclosed earlier are not reiterated for the embodiments of this invention, as the skilled artisan is familiar with e.g. the following basics, provided by a U.S. patent by Vo-Dinh et al. (i.e., U.S. Pat. No. 6,422,998) "Fractal analysis of time varying data," and a wide body of literature. The US Patent by Vo-Dinh et al. taught how to convert data for fractal analysis from one domain to another; in their case from a temporal domain into a spatial domain, such that fractal analysis be performed in the spatial domain, thereby producing a fractal dimension D. sub. F. Their SUMMARY states "The proposed method of Fractal Analysis with Space-Time (FAST) coordinate conversion is based on the concept that, when the temporal signal of a process is converted into a spatial pattern, the element of this spatial pattern can be characterized and analyzed by fractal geometry. This time-space conversion process is consistent with the concept that scale invariance has some parallel in chaos theory, which is generally used to analyze many temporal processes, such as atmospheric turbulence, cardiac rhythms, or mechanical operations. In fact, it has been indicated that chaotic behavior is present in quite a few biological processes that are occurring in the human body, and these give rise to the fractal structures that are prevalent in the body, Goldberg et al., "*Chaos and Fractals in Human Physiology*", *Scientific American*, pp. 43-49, February 1990." The present application uses the methods to make fractal analysis of organisms, such as a Purkinje neuron, not in the physical domain (3D, color), but the dendritic arborization represented in a different domain (2D, black & white). Their methods for even more drastic, but different (time-space) conversion for fractal analysis are elaborated in their Detailed Description of the Invention: "Fractal analysis with space-time coordinate conversion 10 is schematically illustrated in FIG. 1. The input 12 to the process is a time varying electrical signal representing the physical events to be analyzed. For example the input 12 may be a time domain signal produced by medical equipment, such as an electrocardiogram, or by sensors of a manufacturing process wherein the signal represents a time varying phenomenon. The electrical signal is converted at block 14 from the temporal domain into the spatial domain producing a two-dimensional image 16. The results of the temporal to spatial domain conversion are represented by a physical plot on paper or a bit map image of the data can be stored in a computer memory as will be described. The two-dimensional image 16 then is processed by conventional fractal image analysis techniques which produces a fractal dimension DF as the output of the process. The fractal image analysis may be performed using any commercially available software program, such as FractalVision™ licensed by Cedar Software, Wolcott, Vt. U.S.A.)." Citation from Barnsley et al., "A New Class of Markov Processes for Image Encoding," School of Mathematics, Georgia Inst. of Technology Preprint (1980) (Barnsley Markov) is used in the present application to teach how to reduce both DNA and organisms to fractal sets such that they can be statistically correlated, by using the solution of the inverse problem widely known in prior art: "good results are available on the solution of the inverse problem: given a grey-tone image one can say how the maps w, and probabilities p i may be chosen so that the associated iterated function system image is close to the given one [4]. An example of an image computed using a collection of 23 contractive affine maps is given in FIG. 3. Such images may contain infinite detail, which is revealed by refining the partition {bj}; for example, many of the fractals introduced by Mandelbrot [14] can be encoded in this way. The algorithm just described actually computes, in the analytic limit of infinite M, a projection of the invariant measure of a Markov process as described in Section 2. The purpose of this paper is to give the theory behind a more general framework of iterated random maps, such that the maps used need not be contractions, and the associated invariant measure need not be compactly supported. Nonetheless, essentially the same algorithm described above continues to work. The extended theory allows for (a) the inclusion of transformations which take account of symmetries, (b) the inclusion of random irregularities in an image, and (c) the description of images of infinite extent" As they say on page 18, (see line 12) "Our main focus here is on the underlying mathematical structure, which is of interest in its own right". The present application uses their mathematical proof, starting from "3. Proofs" on their page 24 (running through pages 24-32, too extensive to be reiterated in full) as a solid set of equations, theorems, corollaries and proofs, also detailed in the Barnsley et al. patents incorporated by reference in paragraph [0065] to perform the "inverse transformation", to decompose sequences of hereditary material as well as statistically correlated features of organisms to fractal sets. Barnsley et al., "Iterated Function Systems and the Global Construction of Fractals," *Proc. R. Soc. London, A* 399, 243-275 (1985); Barnsley et al., "Solution of an Inverse Problem for Fractals and Other Sets," *Proc. Natl. Acad. Sci, USA*, vol. 83, 1975-1977, April 1986; Barnsley, et al., "Hidden Variable Fractal Interpolation Functions," *School of Mathematics, Georgia Inst. of Technology* (July 1986); Barnsley et al., "Fractal Modeling of Biological Structures, Perspectives in Biological Dynamics and Theoretical Medicine," Koslow, Mandell, Shlesinger, eds., *Annals of New York Academy of Sciences*, vol. 504, 179-194 (1987) (Fractal Modeling); Barnsley et al., "Fractal Modeling of Real World Images", Lecture Notes for Fractals: Introduction, Basics and Perspectives, *SIGGRAPH* (1987); Barnsley, M. F. and Alan D. Sloan, "A Better Way to Compress Images," *BYTE Magazine* (January 1988), pp. 215-223 (A better way); Barnsley, M., Arnaud Jacquin, Francois Malassenet, "Harnessing Chaos for Image Synthesis," *Computer Graphics* 22 (August 1988), pp. 131-140 (Harnessing Chaos); and Barnsley, M. F. and John H. Elton, "A New Class of Markov Processes for Image Encoding," *Adv. Appl. Prob.* 20, 14-32 (1988). These articles describe the mathematics of fractals and fractal analysis in great detail, and are incorporated by reference, as in the parent application.

Preferred embodiments of the invention consider the hereditary material as a fractal object, constituting fractal sets. Furthermore, preferred embodiments of the invention analyze and interpret DNA base-pair sequences as representing a repetitious, fractal language that corresponds to the repetitious, fractal structural and functional properties of cells, organelles, and organs in organisms.

Utilities of preferred embodiments can be best explained by the example of Fractal Model of the Purkinje brain cell. FIG. 3 illustrates a complete circle between the demonstrably fractal neuron of Purkinje cell model, the demonstrably fractal sequences of a guinea pig Purkinje cell) and a sequence of DNA base pairs. The figure of the fractal Purkinje cell model was cited above as "Neural Geometry": Towards a Fractal Model of Neurons, pp. 453-464, in Models of Brain Function, by R. M. J. Cotterill, Cambridge Univ. Press, 1989 and previously incorporated by reference From FIG. 3, FIG. 4, and FIG. 5, it is apparent that the four A, C, T, and G base-pair segments are not identical, they are Closely Similar Repeats (CSR sequences). Therefore, given the assumption that each of the illustrative base-pair segments represent the code for one of the generations of the branch-structure of the Purkinje cell, it is apparent that the base-pair segments can not be identical, since the basic fractal template (B) is not identical to the second generation branching (shown in C, the second generation branchlets are, for instance, smaller). Thus, if one would find a repetitious set of base-pair segments much higher than four (or, in turn, if the four repetitions were not there, only the first segment, the exon) one could detect a pathological morphogenesis of the Purkinje cell possibly leading to neurological disorder. Note, that the most important basic fractal template (shown in B of FIG. 3) is directly related to an (exemplary, not actually identified) base-pair sequence (B). Such a fractal template, which determines the entire character of the arbor, is the conceptual equivalent of an exon. As in fractal structures (should they be arbors of leaves, dendritic branches, arborizations of lung- or coronary arteries of the heart), the subsequent generations, once a main template develops, is a Closely Similar Repetition (CSR) of each branchlet of the main template, with a similar (but smaller) version of the template itself (e.g., see the second, third and fourth generations of the Purkinje neuron model in C, D, E). A preferred embodiment of this invention translates these arborization-generations to the base-pair sequences C, D, E that are not identical to B (and are only CSR-s).

Higher generations of the dendritic (or coronary artery) branches are not the exact replica of the basic template. For instance, branchlets of the second, third and fourth generations are smaller. (Also, in the case of Purkinje neurons, the higher the generation of the dendritic arborization is, the higher is the density of synapses, made of voltage dependent ion-exchanging membrane channels, generated by different genes, on the branchlets. Therefore, it should be expected that the repeated base-pair sequences are not necessarily identical, reflected at the nucleotide-level as CSR-s.) It is a cardinal feature of the embodiment that the mere repetition of a single (protein-producing) gene is not sufficient to build biological organisms (e.g., humans, animals, or plants). For instance, the gene generating a bifurcating protein might be sufficient to grow a basic Purkinje dendritic bifurcation, but once that is done, there must be a mechanism (that does not itself generate proteins) but "links" those gene-combinations that are necessary for generating higher bifurcations, where genes producing the voltage-sensitive ion-exchanger membrane channel proteins must also be brought into play. (This fundamental role of "non-coding DNA sequences" for "assembling gene-combinations" is present in one current biological technique (the SANGAMO technology) to turn genes on and off in laboratory conditions).

FIG. 3 illustrates a fractal model of the Purkinje neuron, as shown in Pellionisz, A. *Neural Geometry: Towards a Fractal Model of Neurons*, in: R. M. J. Cotterill, *Models of Brain Function*, Cambridge Univ. Press, pp. 453-464 (1989), incorporated by reference. The drawing on the left, reproduced from the original, supported a suspicion of Mandelbrot that microscopic organelles such as neurons may show fractal properties. The text field on the right side emphasizes that at the time of constructing the fractal model of neuron (1989) it could only be suspected that one might find later the pertaining fractal sets, determining the fractal neuron: "It must be emphasized, however, that establishing a rigorous relation of these 'code sequences' to the genetic code that underlies the morphogenesis of differentiated neurons may be far in the future" (Pellionisz, 1989).

Figure 5:
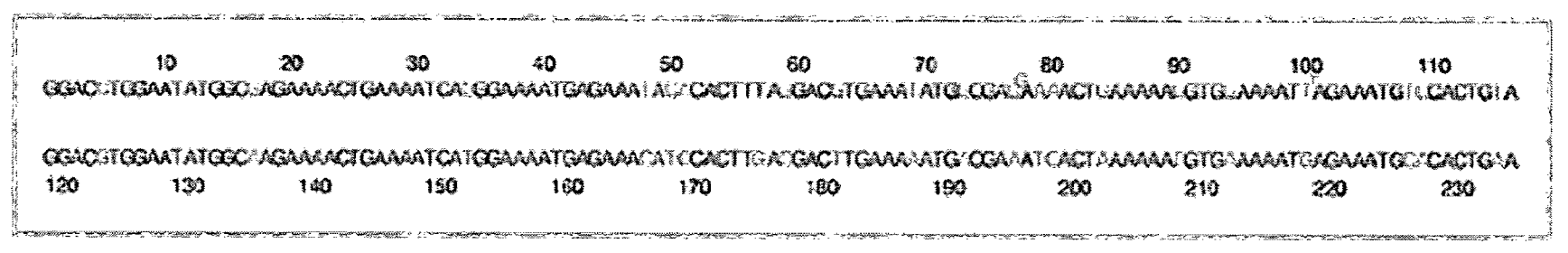
Figure 6:
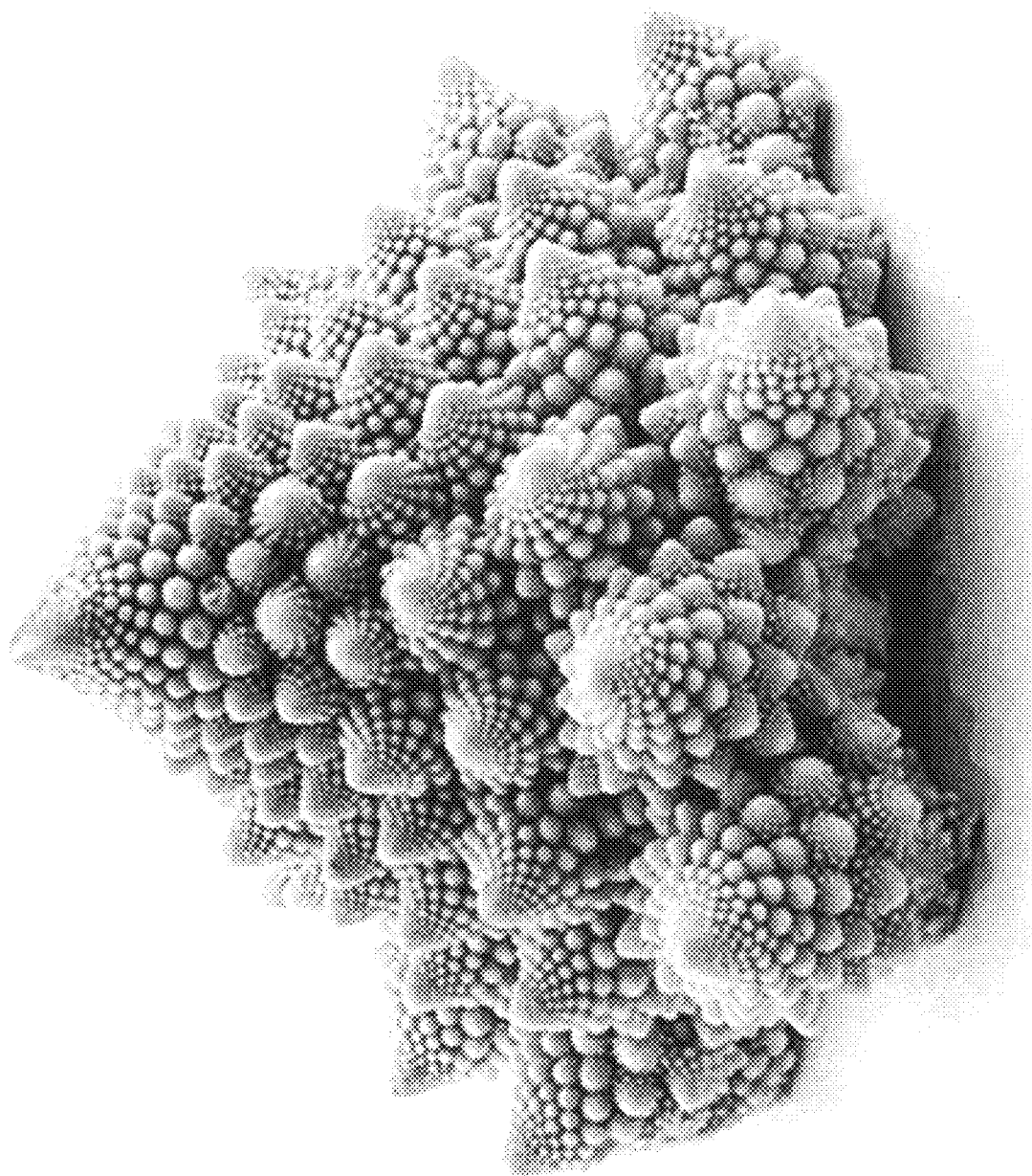
FIG. 6 illustrates the visibly fractal structure of a vegetable (Romanesco broccoli) from the literature

FIG. 3, FIG. 4, and FIG. 5 illustrate CSR Close Repeats in the genetic code of an organism. This is an illustrative example of a DNA base-pair sequence, having only 236 base-pairs (mouse satellite DNA) broken into four CSR segments. The first quarter is refined in subsequent strings. As a core to the invention, further examples are shown in an illustrative manner, that fractal growth can be visually obvious in nature. FIG. 6. illustrates the visually stunningly fractal vegetable Romanesco (Heinz-Otto Peitgen, Hartmut Jürgens, Dietmar Saupe, Evan Maletsky, Terry Perciante (1999) *Fractals for the Classroom: Strategic Activities Volume Three* (Springer Verlag), which is hereby incorporated by reference.

Figure 7:
FIG. 7 illustrates a fractal graphical model of the human lung from the literature.

FIG. 7 illustrates a fractal graphical model of the lung. Similar descriptions are given in the literature also at: Nelson T R, West B J, Goldberger A L. "*The Fractal Lung: Universal and Species-Related Scaling Patterns*" Experientia 1990, volume 46(3) pages 251-254, which is hereby incorporated by reference. This figure from the literature shows that entire organs of the (human) body, such as lungs, exhibit fractal properties. As it can be easily discerned, there are an optimal number of bifurcations, for example in the pulmonary ducts in a given cavity of the chest. Too few bifurcations would not be able to extract enough oxygen for lack of the sufficient active surface. On the other hand, too many bifurcations would result in such a density of ducts that there would be no room for breathing in enough air.

Figure 8:
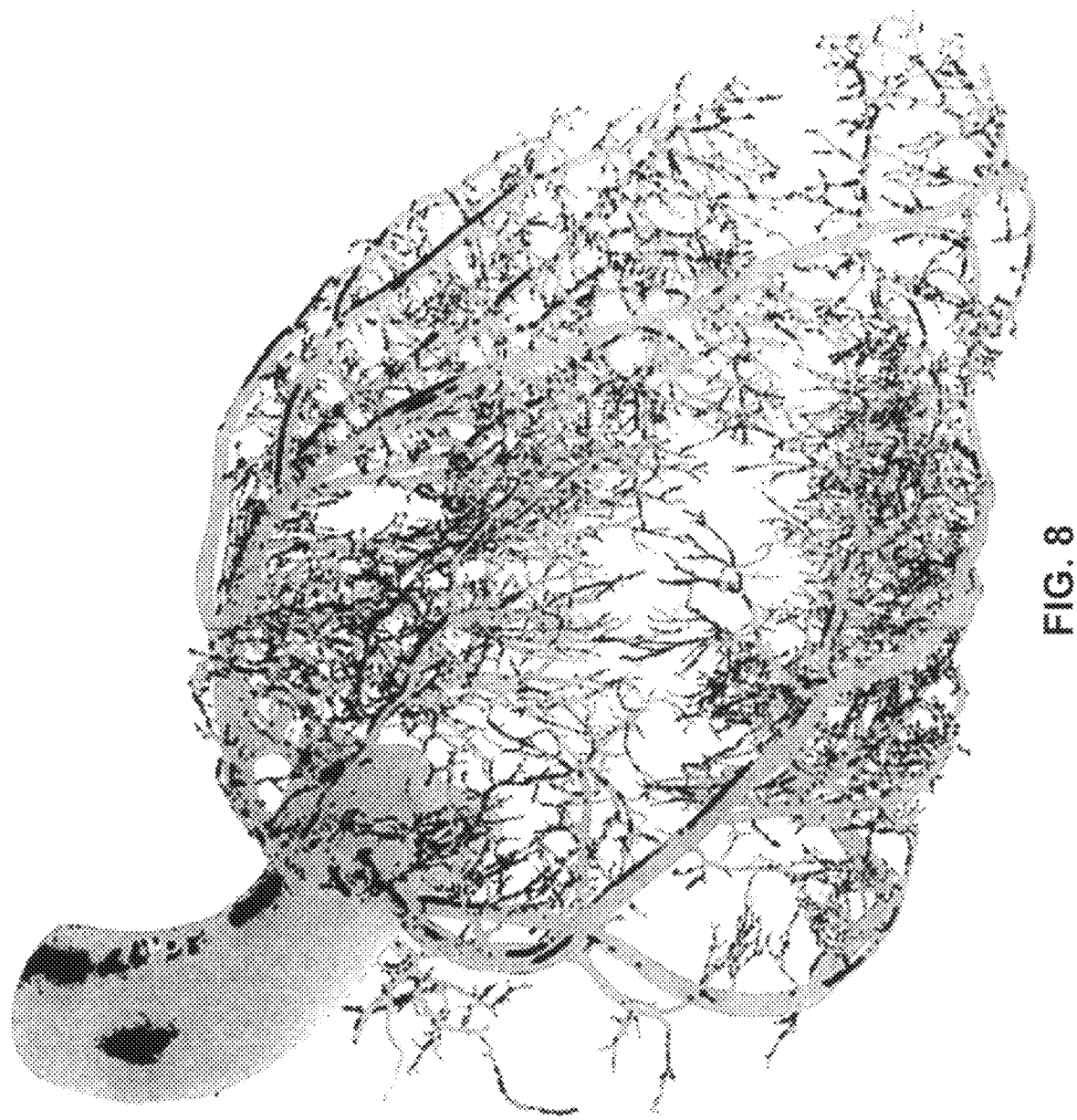
FIG. 8 illustrates a fractal image of the heart coronary, as shown in an 1990 February article of *Scientific American*, "Chaos and Fractals in Human Physiology."

FIG. 8 illustrates a fractal image of the coronary, as shown by Hans van Beek and James B. Bassingthwaighte, University of Washington, on page 46 of *Scientific American*, 1990. February, page 34; "*Chaos and Fractals in Human Physiology*" by Ary L. Goldberger, David R. Rigney and Bruce J. West, which is hereby incorporated by reference. This figure shows that structures over entire organs of the (human) body, such as the coronary arteries of the heart, exhibit fractal properties.

Embodiments of Fractal Methods Connected to Zipf-Mandelbrot Parabolic Fractal Distribution Law: Cerebellar Purkinje Cell Dendritic Tree Model While FIG. 1 show Closely Similar repetitive DNA sequences, the method of relating DNA fractals to Fractals of Organisms is additionally improved in this segment of Specification by teaching the method that reveals that the Fractal Components of the Purkinje Neuron conform to Zipf-Mandelbrot Parabolic Fractal Distribution law.

The first "hints" that the A,C,T,G nucleotide-sequences of DNA (especially of non-coding DNA) possibly harbored a (mathematical) "language" was published before 'the epoch of "massive whole genome sequencing"', reprinted from Flam, Science. 1994 *Hints of a language in junk DNA*.

Figure 10:
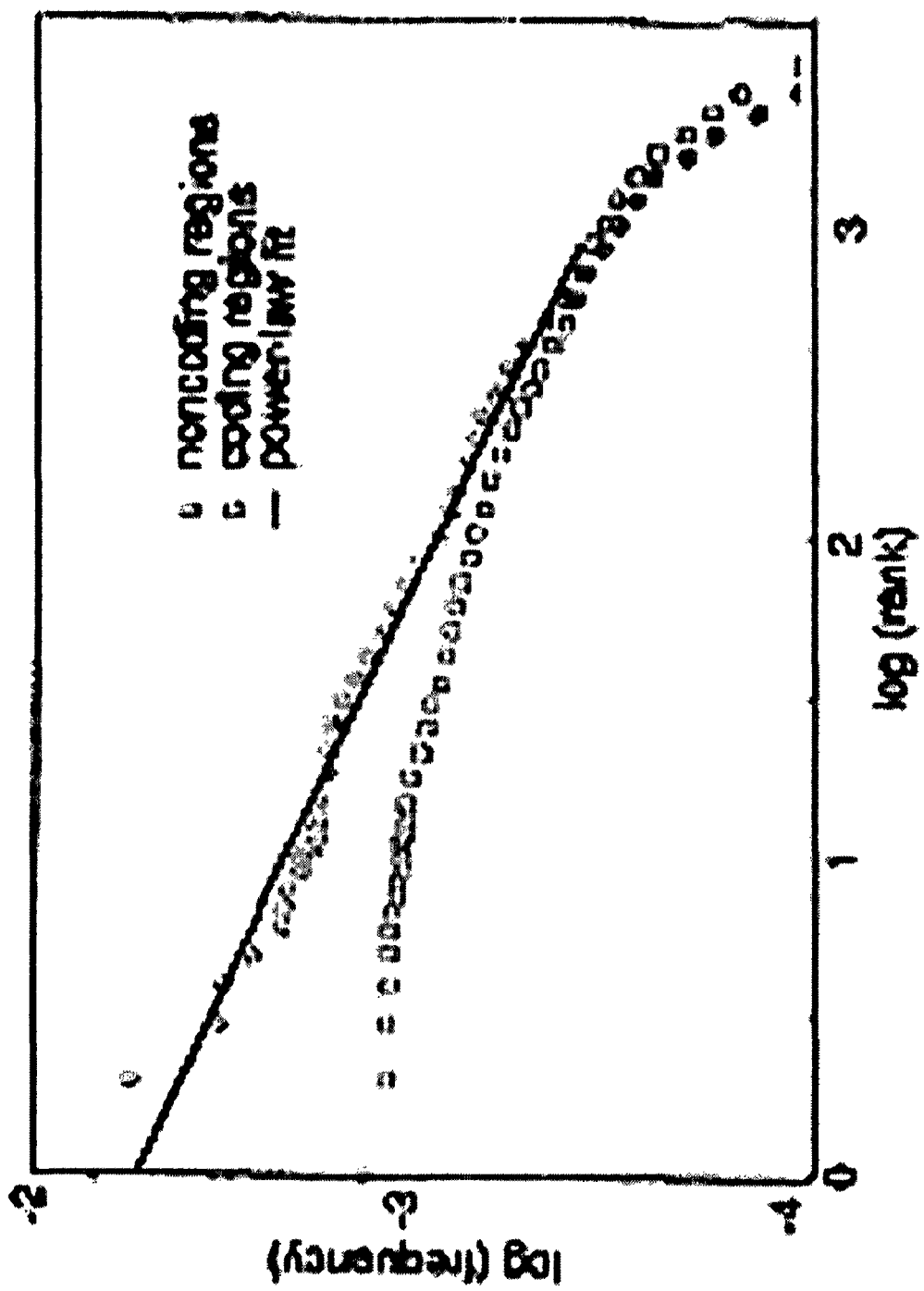
FIG. 10 illustrates that the prior art (Flam, 1994) unsuccessfully attempted to approximate the distribution of repeats in the hereditary material by the linear Zipf-curve.

November 25; 266 (5189):1320, see FIG. 10 (reproduced from FIG. 1., ibid), which is hereby incorporated by reference.

The study reported by Flam was based on a comparison with the empirical "Zipf's law", that applies to natural languages (Zipf, George K, *Human Behaviour and the Principle of Least-Effort*, Addison-Wesley, Cambridge Mass., 1949), which is hereby incorporated by reference. The distribution of frequencies (actual occurrencies) of words in a large corpus of data versus their rank is generally a power-law distribution, with exponent close to one.

Zipf's law is thus an experimental law, not a theoretical one. Zipfian distributions are commonly observed, in many kinds of phenomena. However, the causes of Zipfian distributions in real life are a matter of some controversy, with the DNA as no exception.

While the early observations applied to DNA in 1994 were found worthy of reporting in Science and were widely heralded that "something interesting was lurking in the junk (DNA)", the "Zipf-test" was inconclusive.

Empirical law aside, the biggest problem was the definition of "words" in the DNA. First, Harvard linguistics professor George Kinsgley Zipf (1902-1950) established his "law", based on observations on the English language, in which "words" are taken for granted. He found that in a text the frequency of any word is roughly inversely proportional when plotted against the rank of how common each word was; the frequency of the k-th most common word in a text is roughly proportional to 1/k. Plotting both frequency and rank on a logarithmic scale, "Zipf's law" was expected to yield a declining linear graph also for "words" of the DNA.

When applying this natural language lingustics to DNA the results were not entirely convincing (FIG. 10, reproduced from FIG. 1. of Flam, 1994). Chiefly, not because the graphs did not quite conform with the linear Zipf's law. More importantly, the definition in the noncoding DNA (of the yeast) was completely and explicitly arbitrary, there was no definition of what A,C,T,G strings might constitute "words." In the analysis (conducted by Mantegna, R. N, S. V. Buldyrev, A. L. Goldberger, S. Havlin, C.-.K. Peng and M. Simons, H. E. Stanley., (1994) Linguistic features of noncoding DNA sequences, *Phys Rev Lett* 73, pp. 3169-3172), which is hereby incorporated by reference: "when the group arbitrarily divided up their samples of junk [DNA] into "words" between 3 and 8 bases long and applied the Zipf test, the telltale linear plot emerged."

Looking at FIG. 10. (reproduced FIG. 1 of Flam, 1994), the plot (for non-coding DNA "words", open squares on a log-log scale) starts fairly close to linear, but drops off remarkably at the tail end. The original Flam-diagram of the Zipf-law for DNA was even more controversial when it was applied to the "coding regions" of the DNA (see graph of open circles in FIG. 4, reproduced from FIG. 1. from Flam, 1994). Here, Flam claimed that the Zipf-law "failed"—and the reason cited was that "The coding part [of the DNA] has no grammar—each triplet (of bases) corresponds to an amino acit (in a protein). There's no higher structure to it".

For reasons of illumination of the meaning of Zipf-Mandelbrot Parabolic Fractal Distribution Law of frequency against ranking of repetitions, the fractal structure of cerebellar Purkinje neuron was used, as modeled by Lindenmayer (L-string replacement) fractal algorithm (Pellionisz, 1989, its actual FIG. 6 is partially reproduced below (see FIG. 3.)). Such a structure is determined by the DNA. As to the question if the developing organelle (the Purkinje neuron) is composed of an increasing frequency of higher-order branchlets, is visibly obvious. Swift mathematical analysis reveals a Parabolic Fractal Distribution of the frequency against ranking (on a log-log scale) of the n-th order of branchlets. The number of repetitions in each hierarchy of first (B), second (C), third (D) and fourth (E) generation of branchlets (see table below FIG. 9) follows the same Parabolic Fractal Distribution as it is now found in the whole genome of a free-living organism (See FIG. 11).

Figure 9:
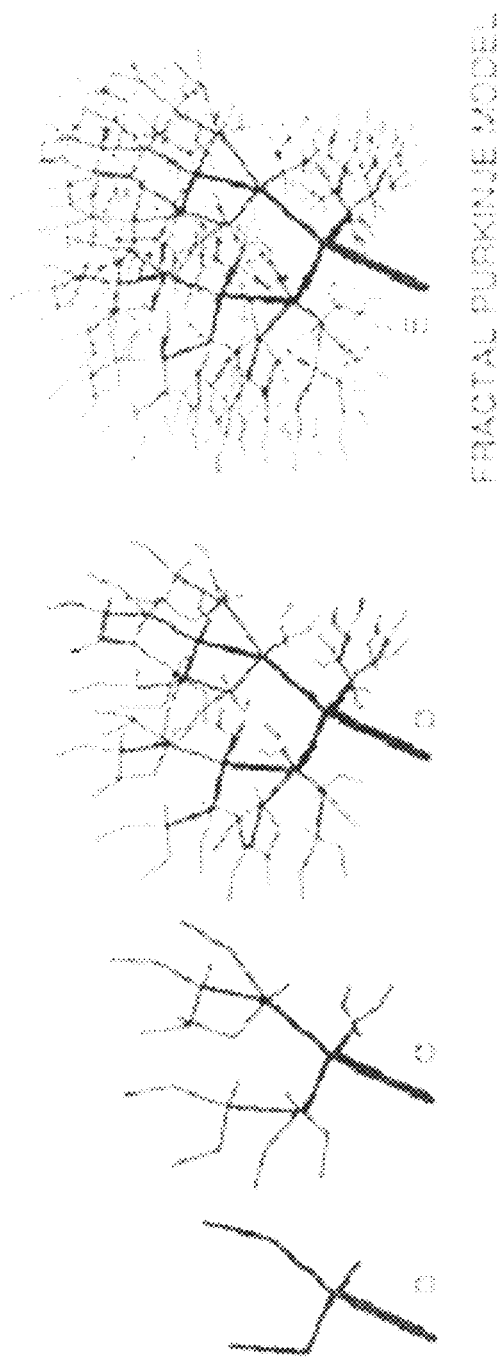
FIG. 9 illustrates that the numbers of Fractal Components of the Purkinje neuron, as it develops, follow the Zipf-Mandelbrot Fractal Parabolic Distribution law.
Figure 11:
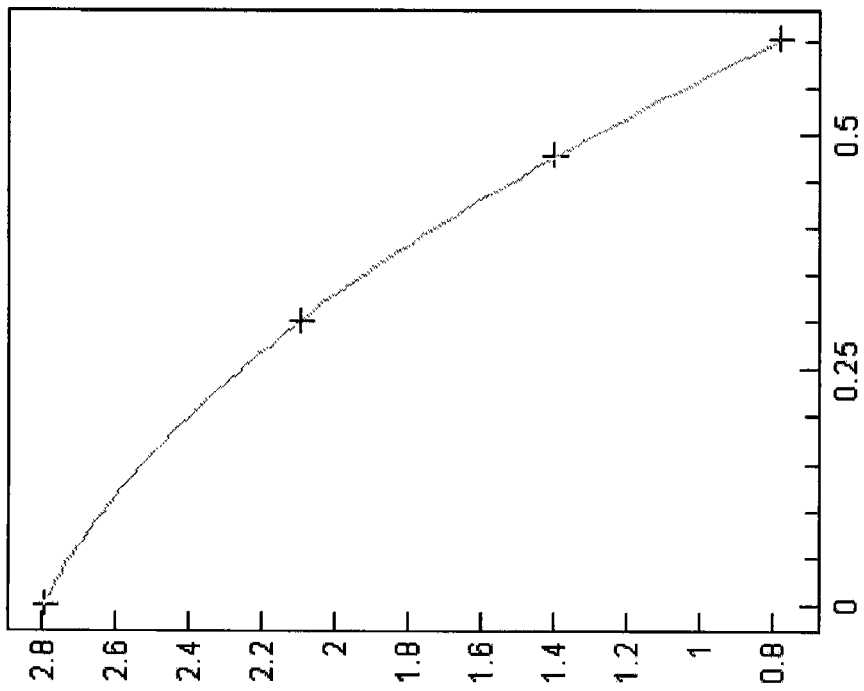
FIG. 11 illustrates that the curve of Fractal Components of the Purkinje neuron, as it develops, follow the Zipf-Mandelbrot Fractal Parabolic Distribution curve.

FIG. 9, FIG. 10, and FIG. 11 show the frequency of occurrence of hierarchical branchlets in the fractal model of a Purkinje neuronal dendritic tree (Pellionisz, 1989). The number of first, second, third and fourth ranking branchlets is 6, 25, 125 and 625, respectively (see FIG. 9). Frequency plotted against rank (log/log scale), perfectly matched by Parabolic Fractal Distribution (see FIG. 11)

Figure 12:
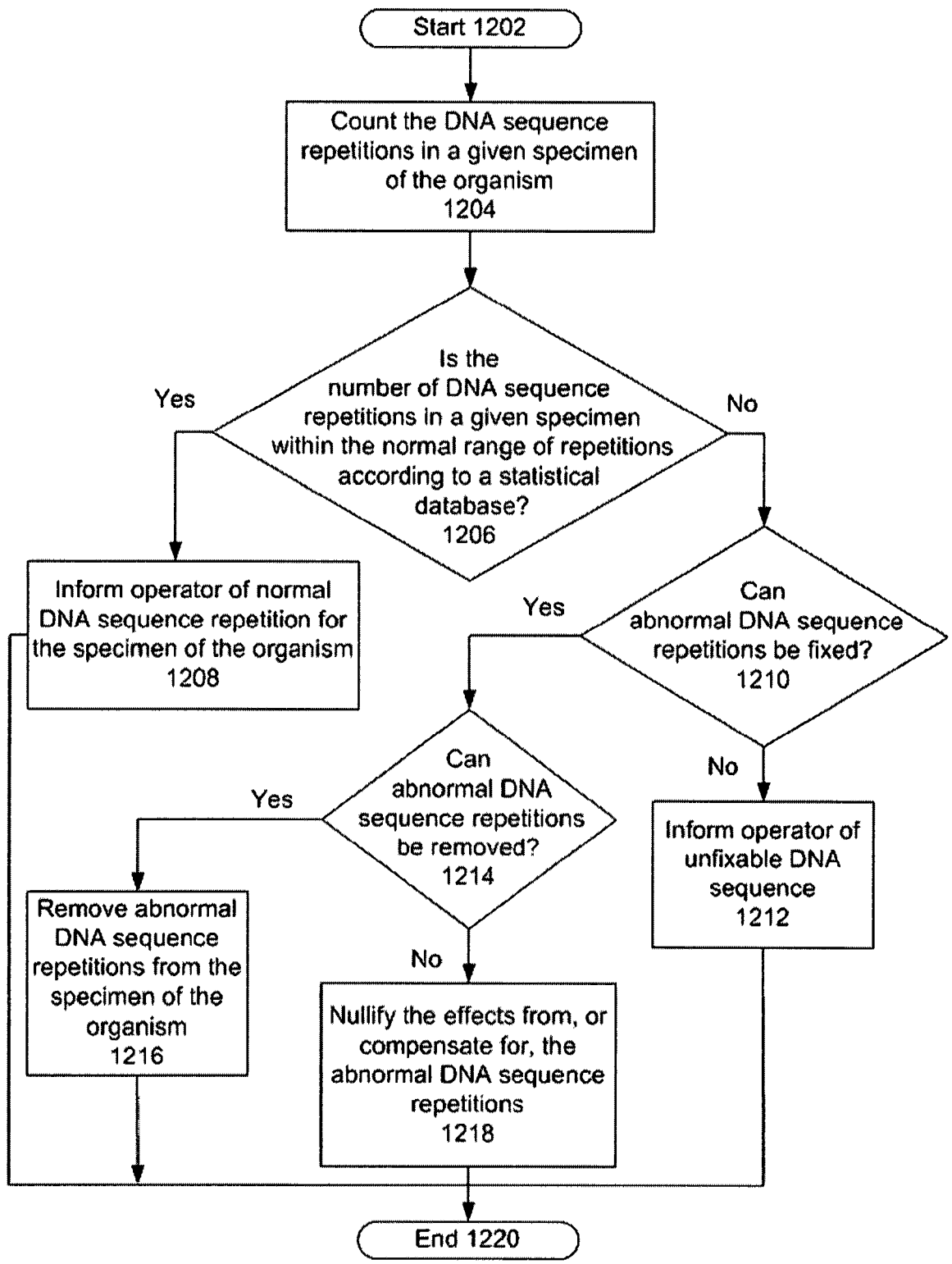
FIG. 12 illustrates a general flowchart for a method to spot, by means of fractal methods, repetitions that are outside of "accepted range", in accordance with one preferred embodiment of the present invention.

FIG. 11 is a log-log plotting of frequency against ranking of Purkinje cell dendritic tree branchlets yields the Parabolic Fractal Distribution expressed by the quadratic polinomial of $y = -3.4107 \times 2 - 1.2995 \times + 2.79608$ A general flowchart is given in FIG. 12 to illustrate the workflow of handling hereditary material such as DNA sequence repetitions themselves, at the start without relating them to fractal properties of the organisms that they govern. This chart will guide the skilled artisan to count repetitions in a given specimen of the organism (1204), in mind of the fact that the invention calls for the use of sequences not only from a single specimen, but from a statistically significant, more than one hundred specimen of a single species. While realizing that at the time of submission this condition is not readily met, methods must be ready for the near future when statistical databases (1206) will be set up enabling analysis, including fractal calculations. Presently, in most cases we do not know if a given closely similar repetition CSR is in the "acceptable range" (normal), or not, and even for ICR ("runs") we only know for a few cases the boundaries of "acceptable range". The embodiments of the invention therefore, rely on the rather rapid development of the field of genomic medicine to report with authority (most notably in PubMed reference publications) if a given number of repeats are associated with preponderance of evidence with particular disorders. Thus, the chart of FIG. 12 will guide the user of fractal methodology based on rapid development of genomic medicine to provide sufficient data, in accordance with one preferred embodiment of the present invention.

Immediate utilization of an embodiment is illustrated in FIG. 13. It provides a flowchart with illustrative examples, for a method to take samples of repetitions (such as depicted in 1301), count CSR Repetitions in hereditary material (1302, in the depicted case the number is 4). Likewise, Fractal Properties of the organism that hereditary material governs to grow, such as fractal complexity (in the depicted case of the Purkinje cell, the number is 4), and other fractal properties (in the depicted case of the Purkinje cell [1303] the skilled artisan will know from FIG. 9 that e.g. the Fractal Component number is 625) can be established. Therefore both fractal objects (the hereditary material in one hand, and the organism it develops, on the other) can be characterized by measurements of Fractal Properties, and thus their correspondence can be established (1305) in accordance with one preferred embodiment of the present invention.

Figure 14:
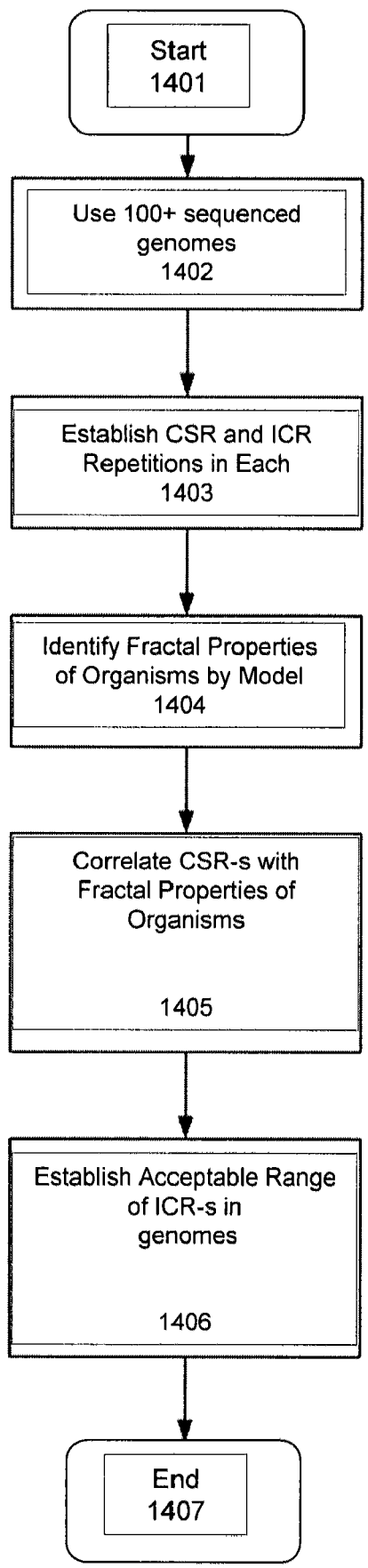
FIG. 14 illustrates a general flowchart for a method to use fractal methods, such as CSR and ICR counts over a statistically significant population of genomes of one species, in accordance with one preferred embodiment of the present invention.
Figure 15:
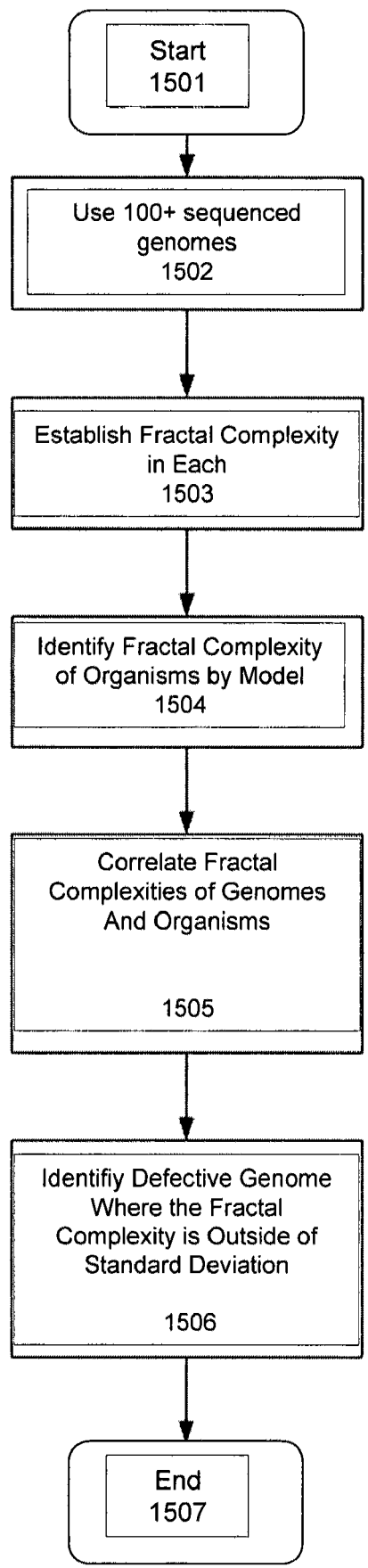
FIG. 15 illustrates new material of establishing fractal complexity in both the hereditary material and in the organism governed by them, and identify defective genomes where the fractal complexity is outside the standard deviation.

FIG. 14 and FIG. 15 illustrate general flowcharts to guide the skilled artisan to proceed with two sets of exemplary Fractal Properties of the hereditary material in relationship to the organism it develops. FIG. 14 is applied to corresponding the Closely Similar Repeats (CSR) and Identical Continuous Repeats (ICR) of the hereditary material to Fractal Properties of the organism the hereditary material governs. In turn, FIG. 15 relates the Fractal Complexity of both the hereditary material and that of the organism that the hereditary material governs. In each flowchart the first step is the start (1401 and 1501, respectively). With the use of 100+ sequenced genomes (1402 and 1502, respectively), the numerical values of CSR-s and ICR-s (1403) and Fractal Complexity (1503) are counted in the hereditary material. The next step (1405 and 1505, respectively) is to correlate the counted Fractal Properties in the hereditary material and in the organism. A most important embodiment of the invention (1406 and 1506) is to compare the counted "problem" values (ICR-s outside the "Acceptable Range", 1406) and Fractal Complexity measures that are outside the standard deviation for 100+ average (1506). The counting and classification procedure thus ends (1407 and 1507, respectively), and a new procedure begins, in accordance with one preferred embodiment of the present invention.

Figure 16:
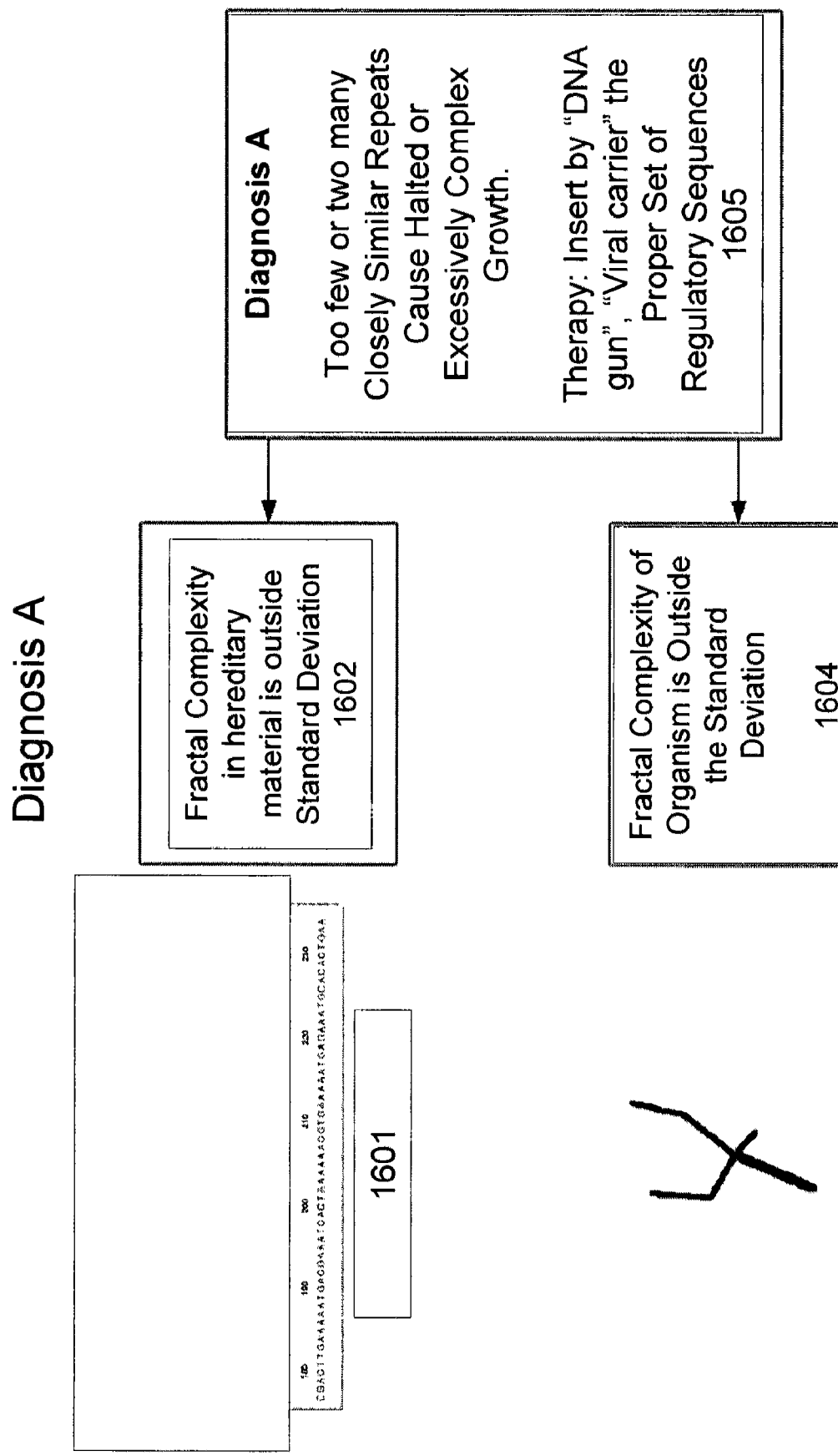
FIG. 16 illustrates a flowchart for a method to provide diagnosis and/or therapy and/or prevention of malformed growth and function based on fractal sets, in accordance with one preferred embodiment of the present invention, with a portion of DNA identified as SEQ. ID. NO. 2 in the CRF file included with the application.
Figure 17:
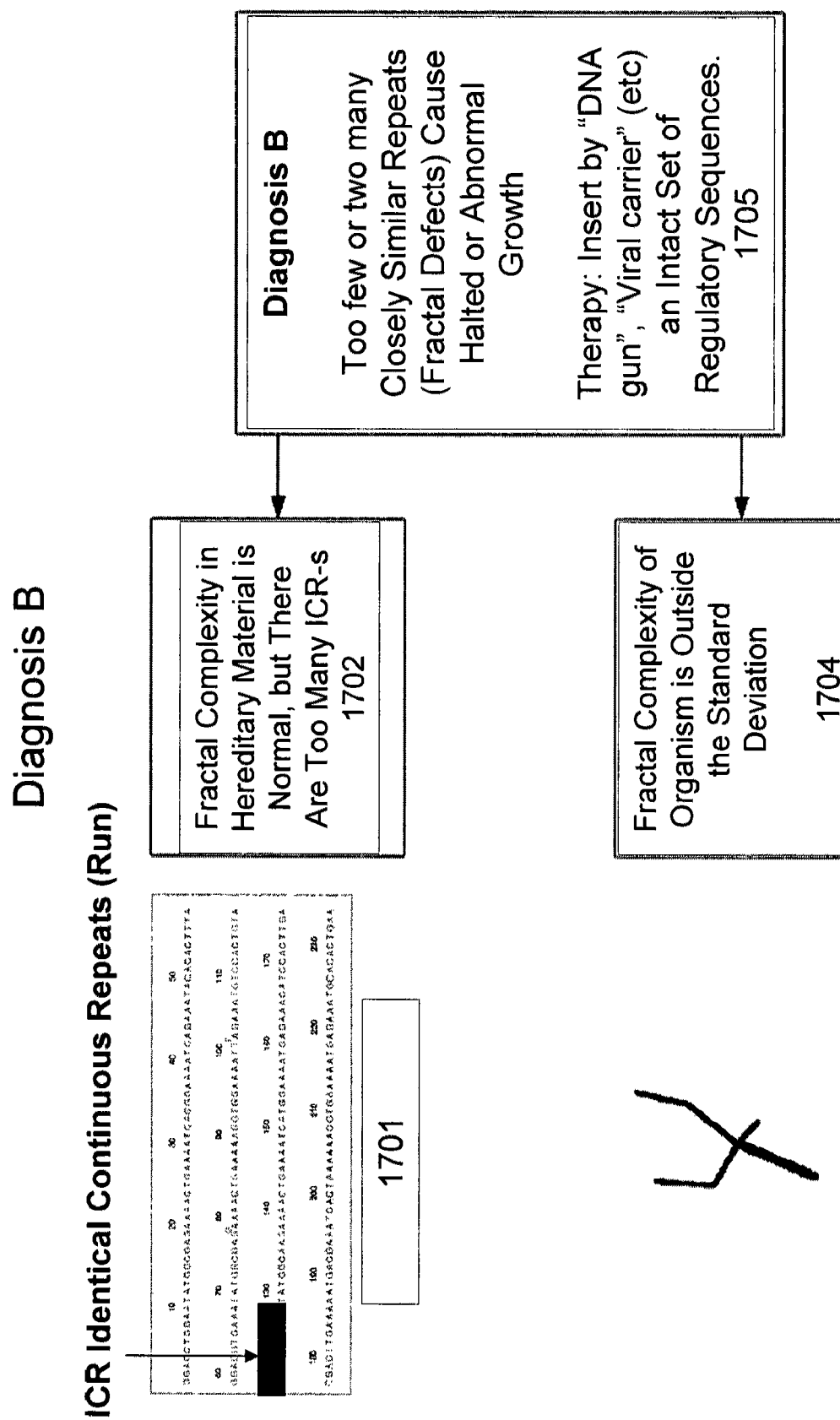
FIG. 17 illustrates a flowchart for a method to provide diagnosis and/or therapy and/or prevention of malformed growth and function in case of the growth halted by Identical Continuous Repeats (Nucleotide "runs"), with a portion of DNA identified as SEQ. ID. NO. 2 in the CRF file included with the application.

FIG. 16 and FIG. 17 show new material of the utility of establishing Fractal Complexity in both the hereditary material and in the organism governed by them, and identify defective genomes where the fractal complexity is outside the standard deviation (1602); where the illustrative example is that only a single CSR is present, with 3 deleted, see 1601; thus the Fractal Complexity of CSR is measured instead of the "average" for 100+, that would be 4.00 with a measured standard deviation that according to the preponderance of PubMed publications is not associated with disease; but the "truncated" set to a measured value of CSR=1.00 would be equivalent to lower vertebrates, where the Purkinje neuron fails to develop its full Fractal Complexity (as seen on 1603, the Fractal Complexity of the organism, in this case the Purkinje cell, is 1.00 instead of the normal average of 4.00). Therefore, "Diagnosis A," as illustrated in FIG. 16, is that the too few Closely Similar Repeats caused a halted growth of the organism. Utility of this invention provides with means with therapy and/or prevention. If, for example, in a plant seed a count of CSR reveals a value outside the standard deviation, known methods that a skilled artisan is familiar with, such as the use of "Gene Gun" (that would not distinguish between inserting "genic" or "non-genic" DNA) or harmless viral carrier, or other methods, available or developed in the future, will be used to supply the seed with the proper (average) set of CSR-s (often called "regulatory sequences"; 1605).

In turn, as shown in FIG. 17, measurements of Fractal Properties, such as in the depicted case the measurements of Fractal Complexity may reveal a "normal" value (1702, in the depicted case the regular 4.00 CSR-s), but the measurement of Identical Continuous Repeats (ICR-s, see 1702) may detect "fractal defects"; defined as nucleotide "runs" (of very short stretches of 2-6 nucleotides followed one after the other, outside the "acceptable range"). Such "runs" entrenched in CSR-s block the utilization of CSR-s and thus result in detectably halted "Fractal Complexity" of the organism that the hereditary material governs (see the "truncated" Purkinje neuron in 1703). Those skilled in the art will know that such "Diagnosis B," as illustrated in FIG. 17, is applicable in case of repeat "Runs" in the genome in case of e.g. Huntington's disease, see an article by Telenius, H., Kremer, B, Goldbert, Y. P. et al., "Somatic and Gonadal Mosaicism of the Huntington Disease Gene: CAG Run Repeat in Brain and Sperm", Nature, Genet, volume 6, pages 409-414 (1994). Huntington's disease belongs to a family of neurological disorders caused by DNA sequences (i.e., a CAG triplet) that tend to be overly repetitive (defined here as outside the "acceptable range"). The "Run" expansion is a kind of stutter in the genome, a repeating short stretch of DNA that runs on and on. The reasons for such over abundant repetitions are not clear, but researchers know that prolonged "Run" repeats can somehow lead to disease. Short phrases of closely similar repetitive DNA (CSR) that encode portions of proteins are common in base-pair sequences. When the Run-repeat expands, however, the extra DNA leads to malformed proteins that clog brain cells or neurons. Huntington's disease is the best known of the 'triplet-repeat' Run-disorders (the repeated DNA "Run" sequence is 'CAG'), but stuttering base-pair sequences also appear to underlie neurological-degenerative diseases known as Friedreich' Spinocerebellar Ataxia. Other diseases are Parkinson's disease, Alzheimer's disease, Recklinghausen's disease, Spongiloform Encephalopathy and Creutzfeld Jakob disease.

"Diagnosis B" by the invented fractal methodology (shown in FIG. 17) results in therapy and/or prevention by the similar insertion of intact sets of CSR-s as in the case of "Diagnosis A", in accordance with one preferred embodiment of the present invention.

Figure 18:
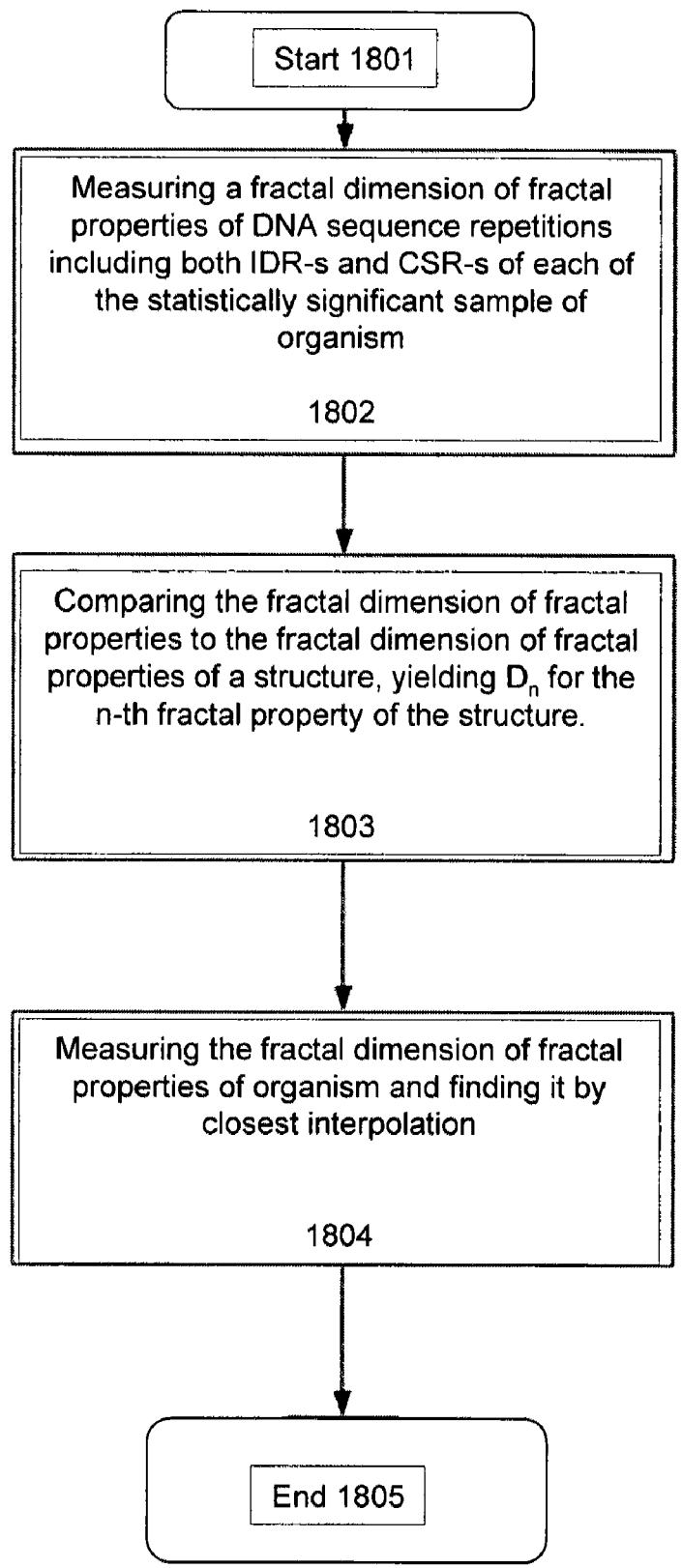
FIG. 18 illustrates a flowchart for using fractal dimension measures both in the hereditary material and in the organism it governs, such that heretofore unknown hereditary material be located by interpolating fractal dimensions, in accordance with one preferred embodiment of the present invention.

FIG. 18 illustrates a flowchart for using fractal dimension measures both in the hereditary material and in the organism it governs, such that heretofore unknown hereditary material be located by interpolating fractal dimensions, in accordance with one preferred embodiment of the present invention. Skilled artisans will be familiar with an assortment of methodologies of measuring Fractal Dimension (defined and the "box-counting method" reiterated above). The key concept here is, that Fractal Dimensions as measured in the CSR-s and IDR-s in the hereditary material may not be the same number as it is in the Organism the hereditary material governs. However, as the database fills up with particular examples as depicted in FIG. 16 between CSR-s governing Purkinje cell growths, their ratios will be used to interpolate for unknown cases. For instance, once the Fractal Dimension of Purkinje Cell arborization (i.e., the branching pattern) is calculated (a particularly easy case for those skilled in the arts), as well as the Fractal Dimension value of CSR-s that govern such growth (such measurement is not known to be available yet), the two values of Fractal Dimensions will define a ratio that is valid for Purkinje neurons. For other brain cells (for instance, for a Pyramidal cell of the cortex) it is likely that a different ratio will apply. As we build up the data-banks with fractal measurements, for a brain cell that is in between Purkinje and Pyramidal neurons (e.g. in Fractal Complexity), the said ratio will be interpolated, and thus the physical measurements of Fractal Properties of Organelles, Organs and Organisms will guide us to locate the hereditary material that is most likely to govern the growth of physical structure or otherwise physically measurable function.

The exemplary embodiments described herein are for purposes of illustration and are not intended to be limiting. Therefore, those skilled in the art will recognize that other embodiments could be practiced without departing from the scope and spirit of the claims set forth below.

What is claimed is:

1. A method to analyze and interpret information inherent in hereditary material of one or more organisms in terms of one or more fractal sets, in relation with one or more resulting fractal structures and one or more fractal functions of said one or more organisms, such that said one or more fractal sets are defined as a superposition over at least two iterations of a fractal template, including:
   using sequenced said hereditary material for said one or more organisms to determine one or more closely similar repetitions (CSR) of one or more DNA sequences in said hereditary material of said one or more organisms;
   identifying one or more fractal structural properties in said one or more organism; and
   finding a plurality of closely similar repetitions (CSR) in said one or more DNA sequences that correspond to said one or more fractal structural or functional properties of said one or more organisms, wherein this step includes using a computer specifically programmed with software to implement the finding of a plurality of closely similar repetitions.

2. The method of claim 1 further including:
   using sequenced said hereditary material for a plurality of specimens of an organism to obtain a statistically significant sample of 100 or more specimens, identifying one or more fractal sets of structural-functional properties in said organism; finding closely similar repetitions (CSR) in said DNA that correspond to said one or more fractal structures of said organism; and
   searching said hereditary material to determine the number of one or more identical continued repeats (ICR) of DNA sequences at one or more locations of said hereditary material falling into the acceptable range and one or more ICR-s that exceed the acceptable range.

3. The method of claim 2 further including fractal complexity:
   using sequenced said hereditary material for a plurality of specimens of an organism to obtain a statistically significant sample of 100 or more specimens, identifying the correlation of fractal complexity of one or more fractal structures of said organism with a number of closely similar repetitions (CSR) in said hereditary material that corresponds to said one or more fractal structures of said organism; and
   searching said hereditary material to determine the number of one or more identical continued repeats (ICR) of DNA sequences at one or more locations in said hereditary material falling into an acceptable range and one or more ICR-s that exceed said acceptable range.

4. The method of claim 1 further including: making a fractal diagnosis of one or more diseases associated with aberrations of one or more fractal sets of said hereditary material, wherein said fractal diagnosis includes an experimental correlation of a first plurality of aberrant numbers of repetitive sequences of hereditary material and a second plurality of an aberrant number of repetitive structural elements of a corresponding organism.

5. The method of claim 4, wherein said structural elements of said corresponding organism are selected from the group of structural elements consisting of: dendritic brain cell bifurcations, cytoskeletal cell bifurcations, and pulmonary organ bifurcations.

6. The method of claim 5, wherein pathological aberrations of fractal complexity of one or more structural elements of dendritic brain cell bifurcations, cytoskeletal cell bifurcations, and pulmonary organ bifurcations can be established as simultaneous with aberrations of the numbers of IDR-s and CSR-s, thus the diagnosis is deduced to aberrant numbers of IDR-s and CSR-s.

7. The method of claim 6, wherein said first plurality of aberrant numbers of repetitive DNA sequences includes a sequence of base pairs selected from the group of DNA sequences, consisting of: a CAG triplet, and a GAA triplet.

8. The method of claim 4, wherein said fractal diagnosis includes experimental correlation of a first plurality of aberrant numbers of repetitive DNA sequences and a second plurality of aberrant numbers of repetitive structural elements of a corresponding organism.

9. The method of claim 4, wherein said fractal diagnosis includes experimental correlation of a first plurality of aberrant numbers of repetitive DNA sequences and a second plurality of aberrant numbers of repetitive structural elements in a dendritic tree of cells of a vertebrate cerebellum, corresponding to Friedreich's Spinocerebellar Ataxia.

10. The method of claim 4, wherein said fractal diagnosis precedes treating with at least one therapy for said second plurality of aberrant numbers of repetitive structural elements of said organism, and said at least one therapy facilitates correction of said second plurality of aberrant numbers of repetitive elements of said organism by removing a plurality of abnormal DNA sequence repetitions from a specimen of said organism.

11. The method of claim 4, wherein said fractal diagnosis precedes treating with at least one therapy for said second plurality numbers exceeding the acceptable range of ICR-s (runs) identical continued repeats of said hereditary material, and at least one therapy facilitates correction of said second plurality of numbers exceeding the acceptable range of ICR-s (runs) identical continued repeats of said organism by nullifying at least one effect from said second plurality of aberrant DNA sequence repetitions.

12. The method of claim 11, wherein said disease is selected from the group of protein agglomeration diseases consisting of: Parkinson's disease, Alzheimer's disease, Huntington's disease, Recklinghausen's disease, Friedreich's Spinocerebellar Ataxia, Spongiloform Encephalopathy and Creutzfeld Jakob disease.

13. The method of claim 4, wherein said fractal diagnosis includes experimental correlation of a first plurality of numbers exceeding the acceptable range of ICR-s (runs) identical continued repeats and a second plurality of aberrant numbers of repetitive elements of said organism causing at least one hereditary disease.

14. The method of claim 1 further including:
   measuring the fractal dimension and one or more fractal properties of one or more DNA sequence repetitions (including both IDR-s and CSR-s) of each of the statistically significant sample of 100 or more specimens of organism, and comparing real number of said fractal dimension and one or more fractal properties to the other real number of a fractal dimension of one or more fractal properties of a structure of said organism, such that the fractal dimension of the n-th sequence repetition is $D_n$ times on average of the fractal dimension of n-th fractal property of the structure; and
   with the use of $D_n$ ratio, measuring the fractal dimension of one or more fractal properties of organism structures without a priori knowing the DNA sequence that generates said structures of said organism, but finding it by searching the genome of said organism for a DNA sequence that numerically closest interpolates the fractal dimension in both the fractal properties of organisms and in the fractal dimension of the IDR or CSR sequence that is searched for.

15. A method to analyze and interpret information inherent in genetic material of one or more organisms in terms of one or more fractal sets, in relation with one or more resulting fractal structures and one or more functions of said one or more organisms, such that said one or more fractal sets are defined as a superposition over at least two iterations of a fractal template, including:
sequencing said genetic material for said one or more organisms to determine one or more self-similar repetitions of one or more DNA sequences in said genetic material of said one or more organisms;
identifying one or more fractal structural properties in said one or more organisms; and
finding a plurality of self-similar repetitions in said one or more DNA sequences that correspond to said one or more fractal structural properties of said one or more organisms, wherein this step includes using a computer specifically programmed with software to implement the finding of a plurality of self-similar repetitions.

16. The method of claim 15 further including:
sequencing said genetic material for a plurality of specimens of an organism to obtain a statistically significant sample to determine an acceptable range of self-similar repetitions of one or more DNA sequences in said genetic material of said organism;
searching said genetic material to obtain a statistically significant sample to determine an acceptable range of repetitions of said one or more DNA sequences in said genetic material of said organism for self-similar repetitions in DNA of said organism;
identifying one or more resulting fractal structures and one or more functions of said one or more organisms in said organism;
finding a plurality of self-similar repetitions in said one or more DNA sequences that correspond to said one or more fractal structures of said organism; and
establishing a statistically significant acceptable range of self-similar DNA repetitions for said organism.

17. The method of claim 15 further including:
measuring a fractal dimension of a sequence repetition of one or more non-coding DNA sequences, and comparing said fractal dimension to a known function of a DNA sequence exon in said organism;
measuring a fractal dimension of a sequence repetition of one or more DNA introns without a correspondingly known DNA sequence exon in said organism; and
searching for a missing DNA sequence exon if said fractal dimension of said sequence repetition of said DNA of said organism is not understood.

18. The method of claim 15 further including:
measuring a fractal dimension and one or more fractal properties of one or more DNA sequence repetitions of one or more introns and one or more exons of a specimen of organism, and comparing said fractal dimension and one or more fractal properties to a fractal dimension and one or more fractal properties of a structure of said organism;
searching for a fractal dimension and one or more fractal properties of organism structures without a known DNA sequence that generates said structures of said organism, and searching said genetic material of said organism for a matching DNA sequence; and
verifying that said matching DNA sequence is a correct DNA sequence that corresponds to said fractal dimension and one or more fractal properties of said structure of said organism.

19. The method of claim 15 further including: making a fractal diagnosis of one or more diseases associated with aberrations of one or more fractal sets of said genetic material, wherein said fractal diagnosis includes an experimental correlation of a first plurality of aberrant numbers of repetitive, self-similar genetic sequences and a second plurality of an aberrant number of repetitive, self-similar structural elements of a corresponding organism.

20. A method to analyze and interpret information inherent in hereditary material of one or more organisms in terms of one or more fractal sets, in relation with one or more resulting fractal structures and one or more fractal functions of said one or more organisms, such that said one or more fractal sets are defined as a superposition over at least two iterations of a fractal template, including:
using sequenced said hereditary material for said one or more organisms to determine one or more closely similar repetitions (CSR) of one or more DNA sequences in said hereditary material of said one or more organisms;
identifying one or more fractal structural properties in said one or more organism;
finding a plurality of closely similar repetitions (CSR) in said one or more DNA sequences that correspond to said one or more fractal structural or functional properties of said one or more organisms, wherein this step includes using a computer specifically programmed with software to implement the finding of a plurality of closely similar repetitions;
using sequenced said hereditary material for a plurality of specimens of an organism to obtain a statistically significant sample of 100 or more specimens, identifying one or more fractal sets of structural-functional properties in said organism; finding closely similar repetitions (CSR) in said DNA that correspond to said one or more fractal structures of said organism; and
searching said hereditary material to determine the number of one or more identical continued repeats (ICR) of DNA sequences at one or more locations of said hereditary material falling into the acceptable range and one or more ICR-s that exceed the acceptable range.

* * * * *

SEQUENCE LISTING

<160> NUMBER OF SEQ ID NOS: 2

<210> SEQ ID NO 1
<211> LENGTH: 885
<212> TYPE: DNA
<213> ORGANISM: Volvox Carteri
<220> FEATURE:
<221> NAME/KEY: seq1
<222> LOCATION: (966)...(1851)
<300> PUBLICATION INFORMATION:
<301> AUTHORS: Duncan, Leonard; Bouckaert, Kristine; Kirk, David L.
<302> TITLE: Kangaroo, a Mobile Element from Volvox Carteri, is a
       Newly Recognized Third Class of Retrotranposons
<303> JOURNAL: Genetics
<304> VOLUME: 162
<305> ISSUE:
<306> PAGES: 1617-1630
<307> DATE: DEC-2002

<400> SEQUENCE: 1

```
atccggaagg ccagccccag cgggtatgct gtcgcgcggc gaagcaccca ggctgatttg      60
ccttgggccg gcaggtttag gtcgcatgca tccggaaggc cagccccagc gggtatgctg     120
tcgcgcagcg aagcacccag gctgatttgc cttgggccgg caggtttagg tcgcatgcat     180
ccggaaggcc agccccaggg ggtatgctgt cgcgcagcga agcacccagg ctgatttgcc     240
ttgcgccggc aggtttaggt cgcatgcatc cggaaggcca gccccagggg gtatgctgtc     300
gcgcagccaa gcacccaggc tgatttgcct tgggccggca ggtttaggtc gcatgcatcc     360
ggaaggccag ccccagggggg tatgctctcg cgcggcgaag cacccaggct gatttgcctt    420
gggccggcag gtttaggtcg catgcatccg gaaggccagc ccaggggggt atgctgtcgc     480
gcaacgaacc acccaggctg atttgccttg gccggcaggt ttaggtcgca tgcatcggaa     540
ggccagcccc agggggtatg ctgtcgcgcg gcgaagcacc caggctgatt tgccttgggg    600
caggtttagg tcgcatgcat ccggaaggcc agccccagcg gtatgctat ccggagtcgc     660 gcagcgaagc acccaggctg atttgccttg gccggcagg tttaggtcgc atgcaggcca     720
gccccagcgg gtatgctgtc gcgcagcgaa gcacccaggc tgatttgcct tgggccggca     780
ggtttaggtc gcatgcatcc ggaaggccag ccccaggggg tatgctctcg cgcggcgaag    840
caccccggct gagttgcctt gggccggcag gtttaggtcg caagt                     885
```

<210> SEQ ID NO 2
<211> LENGTH: 234
<212> TYPE: DNA
<213> ORGANISM: mouse
<220> FEATURE:
<221> NAME/KEY: seq2
<222> LOCATION: (1)...(234)
<300> PUBLICATION INFORMATION:
<301> AUTHORS: Lewin, Benjamin
<302> TITLE: Chapter 4, Clusters and Repeats
<303> JOURNAL: Genes VII
<304> VOLUME:
<305> ISSUE: 7th Edition
<306> PAGES: p. 109, pp. 89-115
<307> DATE: JAN-2000

<400> SEQUENCE: 2

```
ggacctggaa tatggcgaga aaactgaaaa tcacggaaaa tgagaaatac acactttagg      60
acgtgaaata tggcgagaag aactgaaaaa ggtggaaaat ttagaaatgt ccactgtagg     120
acgtggaata tggcaagaaa actgaaaatc atggaaaatg ataaacatcc acttgacgac     180
ttgaaaaatg acgaaatcac taaaaaacgt gaaaatgag aaatgcacac tgaa            234
```